US005584829A

United States Patent [19]

Lavash et al.

[11] Patent Number: 5,584,829
[45] Date of Patent: Dec. 17, 1996

[54] ABSORBENT ARTICLES HAVING PANTY COVERING COMPONENTS THAT NATURALLY WRAP THE SIDES OF PANTIES

[75] Inventors: Bruce W. Lavash, West Chester; Thomas W. Osborn, III, Cincinnati; Robb E. Olsen, Cincinnati; Katherine L. Mayer, Cincinnati; Letha M. Hines, Cincinnati, all of Ohio

[73] Assignee: The Procter & Gamble Company, Cincinnati, Ohio

[21] Appl. No.: 96,121

[22] Filed: Jul. 22, 1993

Related U.S. Application Data

[63] Continuation-in-part of Ser. No. 707,233, May 21, 1991, Pat. No. 5,346,486, Ser. No. 832,246, Feb. 7, 1992, Pat. No. 5,344,416, Ser. No. 915,133, Jul. 23, 1992, Ser. No. 42,840, Apr. 5, 1993, Pat. No. 5,354,400, and Ser. No. 73,256, Jun. 4, 1993, Pat. No. 5,389,094.

[51] Int. Cl.$^6$ .................................................. A61F 13/15
[52] U.S. Cl. .................................... 604/387; 604/385.2
[58] Field of Search .......................... 604/385.1–391, 604/393

[56] References Cited

U.S. PATENT DOCUMENTS

| | | |
|---|---|---|
| 2,787,271 | 4/1957 | Clark . |
| 3,397,697 | 8/1968 | Rickard . |
| 4,166,464 | 9/1979 | Korpman . |
| 4,285,343 | 8/1981 | McNair . |
| 4,589,876 | 5/1986 | Van Tilburg . |
| 4,608,047 | 8/1986 | Mattingly . |
| 4,687,478 | 8/1987 | Van Tilburg . |
| 4,692,163 | 9/1987 | Widlund et al. . |
| 4,790,838 | 12/1988 | Pigneul et al. . |
| 4,891,258 | 1/1990 | Fahrenkrug ........................ 604/385.1 |
| 4,900,320 | 2/1990 | McCoy . |
| 4,911,701 | 3/1990 | Mavinkurve . |
| 4,917,697 | 4/1990 | Osborn et al. . |
| 4,940,462 | 7/1990 | Salerno . |
| 4,950,264 | 8/1990 | Osborn . |
| 5,007,906 | 4/1991 | Osborn et al. . |
| 5,009,653 | 4/1991 | Osborn . |
| 5,037,417 | 8/1991 | Ternstrom et al. . |
| 5,125,918 | 6/1992 | Seidy . |
| 5,129,893 | 7/1992 | Thoren . |
| 5,267,992 | 12/1993 | Van Tilburg ........................... 604/387 |
| 5,281,209 | 1/1994 | Osborn et al. . |
| 5,324,278 | 7/1994 | Visscher et al. . |
| 5,346,486 | 9/1994 | Osborn et al. . |
| 5,354,400 | 10/1994 | Lavash et al. . |
| 5,389,094 | 2/1995 | Lavash et al. . |
| 5,429,630 | 7/1995 | Beal et al. . |
| 5,429,633 | 7/1995 | Davis et al. . |

FOREIGN PATENT DOCUMENTS

| | | |
|---|---|---|
| 0426235A2 | 5/1991 | European Pat. Off. . |
| 0446818A2 | 9/1991 | European Pat. Off. . |
| 0467184A1 | 1/1992 | European Pat. Off. . |
| 0511905A1 | 11/1992 | European Pat. Off. . |
| 0539032A1 | 4/1993 | European Pat. Off. . |
| 40-36391 | 12/1965 | Japan . |
| 236101 | 10/1993 | New Zealand . |
| 2168253 | 6/1986 | United Kingdom . |
| WO92/07535 | 5/1992 | WIPO . |
| WO93/01785 | 2/1993 | WIPO . |
| WO93/01786 | 2/1993 | WIPO . |
| WO93/06805 | 4/1993 | WIPO . |

*Primary Examiner*—Robert A. H. Clarke
*Attorney, Agent, or Firm*—Jeffrey V. Bamber; Steven W. Miller; E. Kelly Linman

[57] ABSTRACT

The present invention relates to absorbent articles such as sanitary napkins, panty liners, and incontinence pads. More particularly, the present invention relates to absorbent articles, such as sanitary napkins, that have longitudinal side edge components that naturally wrap the sides of a wearer's panties which provide an alternative to conventional side flaps.

16 Claims, 13 Drawing Sheets

| | LONGITUDINAL | | | WIDTH | | | FORCE WALL | |
|---|---|---|---|---|---|---|---|---|
| | % LONGITUDINAL STRETCH | g. OF FORCE TO EXTEND PAD | % PAD SET | % WIDTH STRETCH | g. OF FORCE TO EXTEND 1.0" STRIP | % PAD SET | % STRETCH | g. FORCE |
| CONDITIONS FOR STRETCH | 40% | ≤1000 g. ≤800 g. | ≤10 ≤10 ≤25 | 40% | ≤500 g. ≤400 g. | ≤10 ≤25 | 50% | 1500 g. 2000 g. 2500 g. |
| | 25% | ≤800 g. ≤400 g. ≤300 g. | ≤10 ≤25 | 25% | ≤500 g. ≤400 g. | ≤10 ≤25 | 40% | 1500 g. 2000 g. 2500 g. |
| MINIMUM FORCE TO STRETCH | 25% | ≥50 g. | | | | | 25% | 1500 g. 2000 g. 2500 g. |

Table 1...Typical Values for Stretch Parameters

Fig. 7

ABSORBENT ARTICLES HAVING PANTY COVERING COMPONENTS THAT NATURALLY WRAP THE SIDES OF PANTIES

This is a continuation-in-part of the following U.S. patent application: Ser. No. 07/707,233 filed May 21, 1991, now U.S. Pat. No. 5,346,486; Ser. No. 07/832,246 filed Feb. 7, 1992, now U.S. Pat. No. 5,344,416; Ser. No. 07/915,133 filed Jul. 23, 1992, pending; Ser. No. 08/042,840 filed Apr. 5, 1993, now U.S. Pat. No. 5,354,400; and Ser. No. 08/073,256 filed Jun. 4, 1993, now U.S. Pat. No. 5,389,094.

FIELD OF THE INVENTION

The present invention relates to absorbent articles such as sanitary napkins, panty liners, and incontinence pads. More particularly, the present invention relates to sanitary napkins that have longitudinal side edge components that naturally wrap the sides of a wearer's panties which provide an alternative to conventional side flaps.

BACKGROUND OF THE INVENTION

Absorbent articles such as sanitary napkins, pantiliners, and incontinence pads are devices that are typically worn in the crotch region of an undergarment. These devices are designed to absorb and retain liquid and other discharges from the human body and to prevent body and clothing soiling. Sanitary napkins are a type of absorbent article worn by women in a pair of panties that are normally positioned between the wearer's legs, adjacent to the perineal area of the body. Sanitary napkins both with and without side flaps (or wings) are disclosed in the literature and are available in the marketplace. Some particularly preferred sanitary napkins that do not require flaps are described in U.S. Pat. No. 4,950,264 and 5,009,653 issued to Osborn on Aug. 21, 1990 and Apr. 23, 1991, respectively.

Generally when sanitary napkins are provided with flaps, the flaps extend laterally from a central absorbent means and are intended to be folded around the edges of the wearer's panties in the crotch region. Thus, the flaps are disposed between the edges of the wearer's panties in the crotch region and the wearer's thighs. Commonly, the flaps are provided with an attachment means for either affixing the flaps to the underside of the wearer's panties or to the opposing flap. The flaps are particularly effective for preventing exudates from soiling the edges of the wearer's panties.

Sanitary napkins having flaps of various types are disclosed in U.S. Pat. No. 4,687,478, entitled "Shaped Sanitary Napkin With Flaps", which issued to Van Tilburg on Aug. 18, 1987; U.S. Pat. No. 4,608,047, entitled "Sanitary Napkin Attachment Means", which issued to Mattingly on Aug. 26, 1986; U.S. Pat. No. 4,589,876, entitled "Sanitary Napkin", which issued to Van Tilburg on May 20, 1986 and its Reexamination Pat. No. B14,589,876, Certificate of Reexamination issued Apr. 27, 1993; U.S. Pat. No. 4,285,343, entitled "Sanitary Napkin", which issued to McNair on Aug. 25, 1981; U.S. Pat. No. 3,397,697, entitled "Disposable Sanitary Shield For Undergarments", which issued to Rickard on Aug. 20, 1968; and, U.S. Pat. No. 2,787,271, entitled "Sanitary Napkin", which issued to Clark on Apr. 2, 1957.

While sanitary napkins having flaps are commonly viewed as providing better protection against soiling as compared to sanitary napkins without flaps, some women find applying sanitary napkins having flaps to be inconvenient for various reasons. For instance, some women find it to be difficult to attach the flaps to the underside of the crotch of their panties. This can be due to factors such as the tendency for the adhesive fasteners on the flaps to stick to themselves or to other parts of the sanitary napkin. As a result, some women still prefer a sanitary napkin without flaps, and some women who generally prefer a sanitary napkin with flaps, occasionally (such as during periods of light flow) prefer a sanitary napkin without flaps. Therefore, there is a need for a sanitary napkin which provides an alternative to sanitary napkins having conventional side flaps while still providing the protection of side flaps.

In addition, both sanitary napkins with and without flaps are subject to the problem that the wearer's undergarments move with the wearer's movements during wear. These stresses may cause the sanitary napkin to shift from its desired position in the wearer's undergarment. Most sanitary napkins, however, provide no mechanism for adjusting to these movements. This puts stresses on the sanitary napkin and the flaps. The failure to provide the sanitary napkin with a mechanism to adjust to the difference between the movement of the wearer's undergarments and the wearer's body may also cause the sanitary napkin to be not as comfortable as it could be than if it stretched and conformed with the wearer's movements and to the wearer's undergarments.

Several variations of sanitary napkins having conventional flaps that attempt to solve some, but not all of these problems are disclosed in the patent literature. For example, U.S. Pat. No. 4,911,701 issued to Mavinkurve discloses a sanitary napkin having elastic strands for providing a greater convex shape to the body-facing portion of the central absorbent and for enabling adhesive-free placement of the flaps of a winged napkin embodiment into a pair of panties. The sanitary napkin described in this patent, however, still appears to require the user to manipulate the flaps (by first flipping the flaps upward and then placing the flaps in her panties and flipping the flaps back down) since the flaps appear to be pre-disposed to be in a downward folded condition. The Mavinkurve patent also requires that individual elastic strands be attached in a contracted condition to the central absorbent portion of the napkin and/or to its wings or flaps. The napkins described in the Mavinkurve patent can, therefore, be difficult and expensive to manufacture. The Mavinkurve patent also does not disclose any mechanism to account for differences in movement and extensibility of the central absorbent of the napkin and the wearer's panties.

U.S. Pat. No. 4,940,462 issued to Salerno discloses a sanitary napkin with longitudinally expandable flaps. The flaps are designed to fold over the exterior of the wearer's panty and then to expand to conform with the contour of the panties. The Salerno patent, however (in Column 5), appears to require conventional adhesive fasteners to retain the flaps in place on the underside of the wearer's panties. Further, the sanitary napkin shown in the Salerno patent suffers from several drawbacks due to the fact that the longitudinally expandable flaps extend directly outward from the longitudinal sides of the absorbent element. The expandable flaps in Salerno are attached directly to an inextensible body. This limits the extensibility of the portions of the Salerno flaps that are located adjacent to the absorbent element. In order for the Salerno flaps to extend an amount sufficient to wrap around the panty elastics, the flaps have to have a relatively wide transverse dimension. This is shown in FIGS. 3 and 4 of the Salerno reference. The extra flap material can extend too far outward beyond the panty elastics to create a sloppy border that hangs out of the wearer's panties.

Another drawback to the flap construction shown in both the Mavinkurve and Salerno references is that the attachment of the expandable flaps directly to the longitudinal sides of the absorbent element leads to the problem that any compression of the absorbent element will cause the flaps to retract transversely inward. Any bunching of the absorbent element in the sanitary napkins shown in these references, such as that caused by compression by the wearer's legs, causes the flaps to lose their ability to cover a given area of the wearer's panties. The Salerno patent, like the Mavinkurve patent, also does not disclose any mechanism to account for differences in movement and extensibility of the central portion of the napkin and the wearer's panties.

Thus, a need exists for an absorbent article, such as a sanitary napkin, that is provided with an alternative to conventional flaps. In particular, a need exists for a sanitary napkin having an alternative to conventional flaps which provides the protection from soiling of conventional flaps and which can conveniently and efficiently solve the problems caused when attempting to attach conventional flaps to the underside of the wearer's panties and of the failure of the sanitary napkins having conventional flaps to stretch to conform to the wearer's body and the wearer's panties. A need also exists for a sanitary napkin that has a mechanism to adjust to the difference between the movement of the wearer's panties and the wearer's body.

It is, therefore, an object of the present invention to provide an absorbent article, such as a sanitary napkin, that is able to provide coverage to the wearer's panties to reduce side soiling (i.e., staining of the edges of the panty crotch) without the use of conventional flaps.

It is another object of the present invention to provide an absorbent article, such as a sanitary napkin that automatically wraps around the sides of the wearer's panties by the simple action of the wearer pulling up her panties.

It is still another object of the present invention to provide an absorbent article, such as a sanitary napkin, that is able to wrap around the sides of the wearer's panties and stay without providing flaps having panty fasteners thereon, and without attaching separate elastic strands to the sanitary napkin.

It is another object of the present invention to provide an absorbent article, such as a sanitary napkin that has a mechanism for attachment of the sanitary napkin to the wearer's panties that stretches to conform to the wearer's body and the wearer's panties, and responds to the wearer's movements to allow better conformation between the sanitary napkin and the wearer's body and between the sanitary napkin and the wearer's panties.

It is yet another object of this invention to provide an absorbent article, particularly a relatively thin absorbent article, such as a sanitary napkin, that is capable of extending, or more preferably, stretching when the article is worn for improved comfort and fit.

These and other objects of the present invention will be more readily apparent when considered in reference to the following description and when taken in conjunction with the accompanying drawings.

SUMMARY OF THE INVENTION

The present invention provides an absorbent article, such as a sanitary napkin. The sanitary napkin of the present invention has an undergarment covering component (or "panty covering component") that provides coverage to the wearer's panties to reduce side soiling (i.e., staining of the edges of the panty crotch) without the use of conventional flaps.

The sanitary napkin comprises a main body portion comprising a liquid pervious topsheet; a liquid impervious backsheet joined to the topsheet; and an absorbent core positioned between the topsheet and the backsheet. The undergarment covering component (or panty covering component) is joined to the main body portion. The undergarment covering component is wider than the crotch region of the undergarment. The undergarment covering component has a pair of short, flexible (and in some embodiments, drapable) longitudinal side portions (or "side wrapping elements") that extend beyond the crotch edge portions of the wearer's undergarment. The side wrapping elements have a high fold retention. The undergarment covering component comprises at least some extensible portions that are provided with a low return force or no return force (force that tends to cause the extensible portions to retract after they have been extended). Preferably, the extensible portions comprise at least a portion of the undergarment covering component which is located between the affixation points where the undergarment covering component is joined to the main body portion and the distal edges of the side wrapping elements. The fact that the extensible portions are provided with a low return force and the side wrapping elements have a high fold retention allows the side wrapping elements of the undergarment covering component to automatically fold around the crotch edge portions of the wearer's undergarment toward the underside of the undergarment and to remain so folded when the absorbent article is placed in an undergarment and the undergarment is pulled up adjacent the wearer's body.

The extensible portions of the undergarment covering component may comprise any type of extensible structure, including materials that have an inherent extensibility and materials that are gathered, pleated, or otherwise formed into extensible structures. These portions can be extensible in the longitudinal direction, the transverse direction, or both. The undergarment covering component can comprise a laminate of one or more nonwoven materials and an elastomeric film. In one alternative version of this laminate embodiment, the elastomeric film can be present in all but the four regions of the laminate where the periphery of the undergarment covering element intersects with the edges of the wearer's panty crotch. In other embodiments, the undergarment covering component can be extensible only in these four regions and inextensible everywhere else.

A non-limiting number of additional variations of the undergarment covering component are described herein. For instance, the undergarment covering component can comprise the backsheet of the sanitary napkin. In still other embodiments, the sanitary napkin can comprise an undergarment covering component which is a separate element that is attached to the main body portion of the sanitary napkin at spaced apart attachment zones. The undergarment covering component is unattached to the main body portion between the attachment zones to provide unattached portions of the undergarment covering component in the central region of the main body portion. The unattached portions of the undergarment covering component are capable of separating from the main body portion so that the main body portion of the sanitary napkin can stay in contact with the wearer's body and the undergarment covering component can stay attached to the wearer's panties even when the panties pull away from the wearer's body during wear.

In variations of this latter embodiment, the undergarment covering component can be joined to the main body portion of the sanitary napkin by material that has slack built into it by providing flaccid material, pleated material, extensible material, or the like between the main body portion and the undergarment covering component. Numerous other variations are possible. For example, the sanitary napkin of the present invention may comprise a main body portion that has its longitudinal side margins folded inward underneath the main body portion of the sanitary napkin and the longitudinal side margins attached to an extensible panty covering component that extends outward beyond the longitudinal side margins of the main body portion. In still another embodiment, the sanitary napkin comprises an extensible main body portion (including an extensible topsheet that is attached to an extensible backsheet which extends beyond the longitudinal edges of the absorbent core).

The sanitary napkin of the present invention provides an alternative to sanitary napkins having conventional side flaps for several reasons. The undergarment covering component does not extend far enough outward beyond the side edges of the wearer's panties to cause any inconvenience to the wearer. The undergarment covering component requires no action on the part of the wearer to fold the side wrapping elements under her panties or to attach the same to her panties. The undergarment covering component stays in place well enough to cover the sides edges of the wearer's panties without affixing it to the outside surface of the panties.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

FIG. 7 is a table which shows preferred relationships between the magnitude of stretching forces applied to the sanitary napkin and the amount the sanitary napkin stretches in response to such forces.

DETAILED DESCRIPTION OF THE INVENTION

1. General Characteristics of the Absorbent Article

The overall characteristics of the absorbent article of the present invention will be discussed first.

FIGS. 1–5 show a preferred embodiment of a disposable absorbent article of the present invention 20. The present invention relates to absorbent articles, such as sanitary napkins. More particularly, the present invention relates to sanitary napkins that have a main body portion 21 (or "basic sanitary napkin" or "base sanitary napkin") that comprises the portions of the sanitary napkin without the undergarment covering component, and an undergarment covering component ("garment covering component", or "panty covering component") 100 that preferably stretches with the wearer's panties and automatically wraps the sides of the wearer's panties when the wearer places the sanitary napkin in her panties and pulls her panties up.

The term "absorbent article", as used herein, refers to articles which absorb and contain body exudates. More specifically, the term refers to articles which are placed against or in proximity to the body of the wearer to absorb and contain the various exudates discharged from the body. The term "absorbent article" is intended to include sanitary napkins, pantiliners, and incontinence pads (and other articles worn in the crotch region of a garment). The term "disposable" refers to articles which are intended to be discarded after a single use and preferably recycled, composted, or otherwise disposed of in an environmentally compatible manner. (That is, they are not intended to be laundered or otherwise restored or reused as an absorbent article.) In the preferred embodiment illustrated, the absorbent article is a sanitary napkin designated 20.

The term "sanitary napkin", as used herein, refers to an article which is worn by females adjacent to the pudendal region that is intended to absorb and contain the various exudates which are discharged from the body (e.g., blood, menses, and urine). It should be understood, however, that the present invention is also applicable to other feminine hygiene or catamenial pads such as panty liners, or other absorbent articles such as incontinence pads, and the like.

Figure 1:
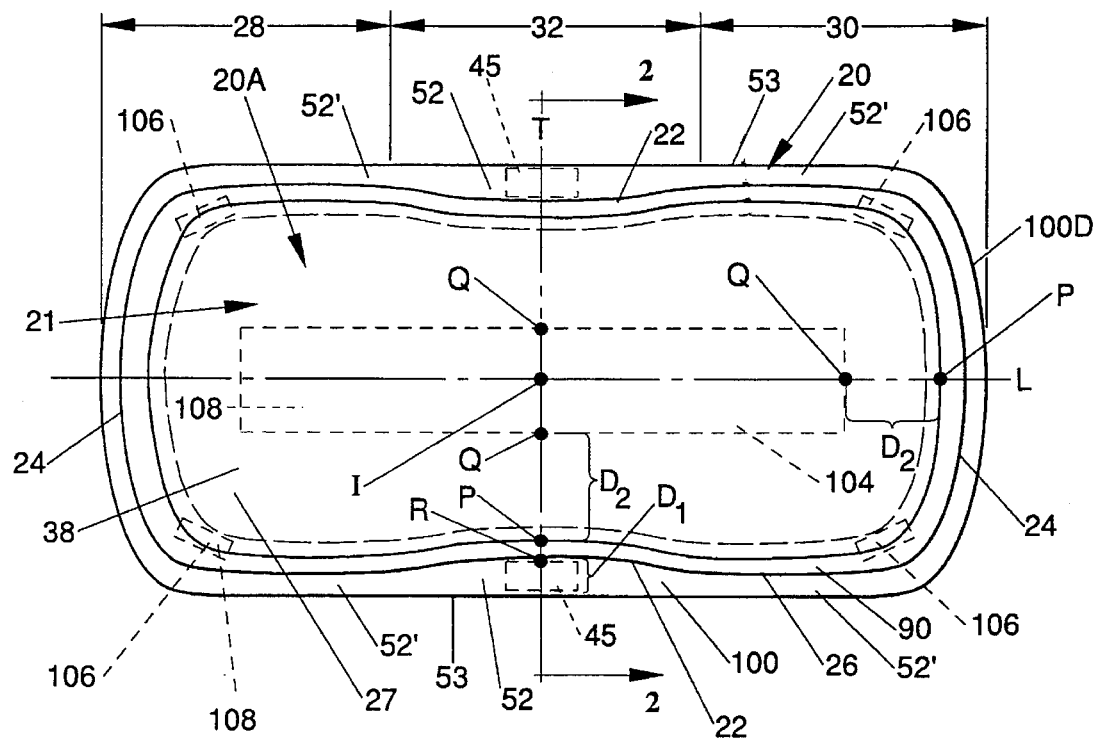
FIG. 1 is a top plan view of a preferred embodiment of the sanitary napkin of the present invention.

The sanitary napkin 20 has two surfaces, a liquid pervious body-contacting surface or "body surface" 20A and a liquid impervious garment surface 20B. The sanitary napkin 20 is shown in FIG. 1 as viewed from its body surface 20A. The body surface 20A is intended to be worn adjacent to the body of the wearer. The garment surface 20B of the sanitary napkin 20 (shown in FIG. 2) is on the opposite side and is intended to be placed adjacent to the wearer's undergarments when the sanitary napkin 20 is worn.

The sanitary napkin 20 has two centerlines, a longitudinal centerline L and a transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction.

FIG. 1 shows that the main body portion 21 of the sanitary napkin 20 has two spaced apart longitudinal edges 22, two spaced apart transverse or end edges (or "ends") 24, and four corners 27, which together form the periphery 26 of the main body portion of the sanitary napkin 20. The main body portion also has two end regions, which are designated first end region 28 and second end region 30. A central region 32 is disposed between the end regions 28 and 30. The end regions 28 and 30 extend outwardly from the edges of the central region 32 about ⅛ to about ⅓ of the length of the main body portion. A detailed description of the central region 32 and the two end regions 28 and 30 is contained in U.S. Pat. No. 4,690,680 issued to Higgins on Sep. 1, 1987.

The sanitary napkin 20 (or main body portion thereof) can be of any thickness, including relatively thick, relatively thin, or even very thin. The embodiment of the sanitary napkin 20 shown in FIGS. 1–3 of the drawings is intended to be an example of a relatively thin sanitary napkin, preferably an "ultra-thin" sanitary napkin. It should be understood, however, when viewing these figures the number of layers of material shown cause the sanitary napkin 20 to appear much thicker than it actually is. An "ultra-thin" sanitary napkin 20 as described in U.S. Pat. Nos. 4,950,264 and 5,009,653 issued to Osborn preferably has a caliper of less than about 3 millimeters. The thin sanitary napkin 20 shown should also be preferably relatively flexible, so that it is comfortable for the wearer.

Figure 2:
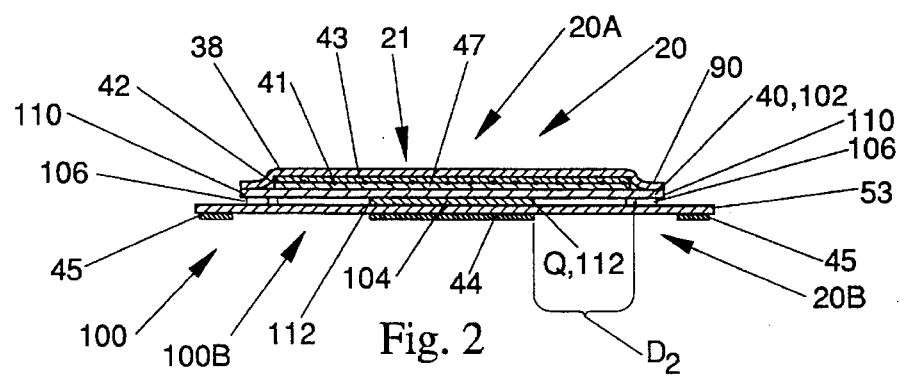
FIG. 2 is a schematic sectional view taken along line 2—2 of the sanitary napkin shown in FIG. 1.

FIG. 2 shows the individual components of the main body portion 21 of the sanitary napkin 20 of the present invention. The main body portion 20 shown in FIG. 2 generally comprises at least three primary components. These include a liquid pervious topsheet 38, a liquid impervious backsheet (or "barrier means") 40, and an absorbent core 42 positioned between the topsheet 38 and the backsheet 40. There are occasions, however, when one or more of these components, such as the backsheet, can be replaced by a component that serves as part of the undergarment covering component described below. The main body portion 21 of the sanitary napkin 20 can be comprised of mostly conventional components, and as a result, be generally inextensible. In preferred embodiments, however, main body portion of the sanitary napkin is one of those described in U.S. patent application Ser. Nos. 07/915,133 and 07/915,284 both filed Jul. 23, 1992, in the name of Osborn, et al. (PCT Publication Nos. WO 93/01785 and 93/01786 both published Feb. 4, 1993), which is comprised of one or more extensible components. More preferably, the main body portion 21 is comprised of all extensible components, and the sanitary napkin has an overall extensibility.

The sanitary napkin 20 of the present invention also comprises a panty covering component 100. The panty covering component 100 comprises a pair of side wrapping elements 52 that extend laterally outward beyond the longitudinal side edges 22 of the main body portion 21 a distance of less than one-half the width of the main body portion to the distal edges 53 of the side wrapping elements 52. At least portions of the panty covering component 100 are extensible. The extensible portions of the panty covering component 100 should generally be located between the points where the panty covering component is attached to the main body portion, Q, and the distal edges 53 of the side wrapping elements 52. The side wrapping elements 52 are the portions of the panty covering component 100 that will automatically fold around the crotch edge portions of the wearer's panties toward the underside of the panties when the sanitary napkin is placed in the wearer's panties and the panties are pulled up adjacent the wearer's body.

Figure 6:
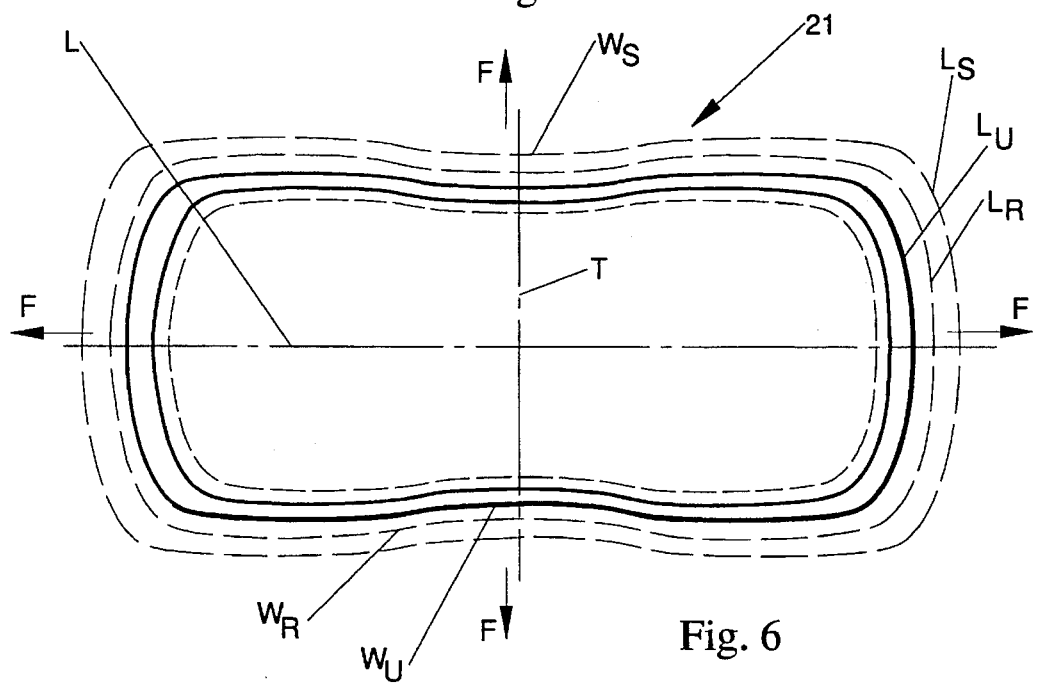
FIG. 6 is a top plan view showing the extensibility of the main body portion of the sanitary napkin shown in FIG. 1.

The extensibility of the main body portion 21 of the sanitary napkin 20 is shown in a simplified fashion in FIG. 6. The term "extensible", as used herein, refers to articles that can increase in at least one of their dimensions in the x-y plane. The x-y plane is a plane generally parallel to the faces of the sanitary napkin 20. The main body portion 21 of the sanitary napkin 20 shown in FIG. 6 is preferably extensible both in length and width. The main body portion 21 of the sanitary napkin 20, in other embodiments however, may only be extensible in one of these directions. Preferably, the main body portion of the sanitary napkin 20 is extensible at least in the longitudinal direction.

The main body portion 21 of the sanitary napkin 20 may in some preferred embodiments, in addition to being extensible, also be stretchable. The term "stretchable", as used herein, refers to articles that are extensible when stretching forces are applied to the article and offer some resistance to stretching. More preferably still, the main body portion 21 of the sanitary napkin 20 may be elastically stretchable. The terms "elastically stretchable" or "elastically extensible" are intended to be synonymous. These terms, as used herein, mean that when the stretching forces are removed, the main body portion will tend to return toward its unextended or unstretched (or "original" dimensions). The main body portion 21 need not return all the way to its unstretched dimensions, however. It may, as shown in FIG. 6, return to relaxed dimensions (such as $L_R$ and $W_R$) between its unstretched dimensions and extended (or stretched dimensions) $L_S$ and $W_S$. Making the main body portion 21 elastically stretchable will reduce the undesirable tendency of the main body portion to gather longitudinally inward (i.e., bunch longitudinally) when forces which tend to stretch the sanitary napkin are removed. This is particularly true when the wearer's panties contract.

The main body portion of the sanitary napkin is preferably extensible in the amounts described in PCT Publication Nos. WO 93/01785 and WO 93/01786. To summarize the same, the main body portion is preferably capable of extending between about 5% and less than about 50%, more preferably between about 10% and about 40%, and most preferably between about 25% and about 40% under the forces associated with wearing the sanitary napkin in a pair of panties. Preferably, the main body portion is capable of such extension under forces of between about 50–100 grams and about 1,000–1,500 grams, more preferably under forces of between about 250 grams and about 800 grams. FIG. 7 is a table which sets forth some additional ranges of forces for the extensibility of preferred absorbent articles. It is to be understood that all of the limits and ranges specified herein include all narrower ranges, limits, and amounts that are within the specified limits and ranges. As shown in FIG. 7, the main body portion of the sanitary napkin can also be provided with a "force wall" to prevent elongation past a certain amount without substantial increases in the amount of force applied to the main body portion. If the panty covering component is provided with an extensible portion that is fastened to the inside of the wearer's panty crotch, then the panty covering component is preferably also provided with a force wall to facilitate removal of the sanitary napkin from the wearer's panties.

The extensible portions of the panty covering component preferably are extensible in similar amounts, and in response to similar forces, as the portions of the sanitary napkin comprising the main body portion. However, any inherent elasticity in the extensible portions of the panty covering component (that is, any tendency of the extensible portions to return to their original dimension) is generally relatively low. The extensible portions are also preferably extensible without being elasticized or elsaticated (where separate elastic bands are stretched and attached to the panty covering component in an extensible condition). These extensible portions of the panty covering component have a relatively high "set" (compared to the values shown in FIG. 7) and a low return force so they will wrap around the edges of the wearer's panties without tending to come unwrapped from the same.

2. The Individual Components of the Sanitary Napkin and the Assembly of the Same.

Figure 3:
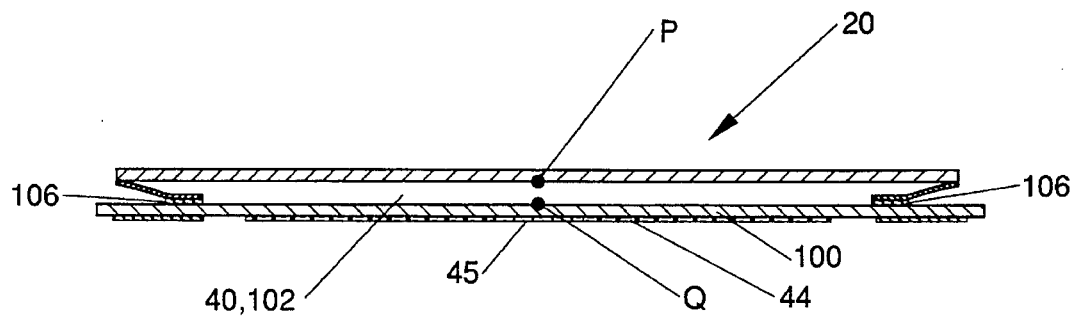
FIG. 3 is a side view of the sanitary napkin shown in FIG. 1 shown before use.

The individual components which may be suitable for the various embodiments of the sanitary napkin 20 of the present invention will now be looked at in greater detail with reference to FIGS. 1–3.

A. The Topsheet

The topsheet 38 comprises a first liquid pervious component. When the sanitary napkin 20 is in use, the topsheet 38 is in close proximity to the skin of the user. The topsheet 38 is preferably as compliant, soft feeling, and non-irritating to the user's skin as possible. The topsheet 38 should further exhibit good strikethrough and a reduced tendency to rewet, permitting bodily discharges to rapidly penetrate it and flow toward the core 42, but not allowing such discharges to flow back through the topsheet 38 to the skin of the wearer.

The topsheet 38 has two sides (or faces or surfaces), including a body-facing side 38A and a garment-facing side (or core-facing side) 38B. The body-facing side 38A of the topsheet 38 generally forms at least a portion of the body-contacting surface ("body surface") 20A of the sanitary napkin 20. The topsheet 38 has two longitudinal edges 38C and two end edges 38D.

(A similar numbering system applies to the other components of the sanitary napkin. That is, the side of the component facing the wearer's body can be designated by the number of the component and a reference letter "A". The side facing the wearer's undergarments can be designated by the number of the component and the letter "B". The side and end edges can be designated by the number of the component and the reference letters "C" and "D", respectively.)

A suitable topsheet 38 may be manufactured from a wide range of materials including, but not limited to woven and nonwoven materials, apertured formed thermoplastic films, apertured plastic films, hydro-formed films, porous foams, reticulated foams, reticulated thermoplastic films, and thermoplastic scrims. Suitable woven and nonwoven materials can be comprised of natural fibers (e.g., wood or cotton fibers), synthetic or modified natural fibers (e.g., polymeric fibers, such as polyester, polypropylene fibers, and polyethylene, or polyvinylalcohol, starch base resins, polyurethanes, cellulose esters, nylon, and rayon fibers) or from a combination of natural and synthetic fibers. When the topsheet 38 comprises a nonwoven web, the web may be spunbonded, carded, wet-laid, meltblown, hydroentangled, combinations of the above, or the like.

Apertured films are generally preferred for the topsheet 38 because they are pervious to liquids and, if properly apertured, have a reduced tendency to allow liquids to pass back through and rewet the wearer's skin. Suitable apertured films are described in U.S. Pat. No. 3,929,135 issued to Thompson on Dec. 30, 1975, U.S. Pat. No. 4,324,426 issued to Mullane et al. on Apr. 13, 1982, U.S. Pat. No. 4,342,314 issued to Radel et al. on Aug. 3, 1982, U.S. Pat. No. 4,463,045 issued to Ahr, et al. on Jul. 31, 1984, and U.S. Pat. No. 5,006,394 issued to Baird on Apr. 9, 1991. A particularly suitable topsheet 38 is made in accordance with U.S. Pat. No. 4,342,314 issued to Radel and U.S. Pat. No. 4,463,045 issued to Ahr, et al. A topsheet 38 made of model X-3265 or model P1552 apertured formed film sold by Tredegar Corporation of Terre Haute, Indiana has been found to work well.

The topsheet 38 can be made extensible by performing a mechanical operation, such as pleating, corrugating, or ring rolling on the topsheet material to provide folds in the topsheet that are able to open when the topsheet is stretched. Such a process can be performed on many of the topsheet materials described above. In one preferred embodiment of the present invention, the topsheet 38 is made in accordance with U.S. Pat. No. 4,463,045 and ring rolled to provide it with a degree of extensibility. Such a topsheet is described in U.S. patent application Ser. No. 07/936,195 entitled "Polymeric Web Having Deformed Sections Which Provide A Substantially Increased Elasticity To The Web", filed in the name of John J. Curro, et al. on Aug. 25, 1992.

Suitable processes for ring rolling or "pre-corrugating" are described in U.S. Pat. No. 4,107,364 issued to Sisson on Aug. 15, 1978, U.S. Pat. No. 4,834,741 issued to Sabee on May 30, 1989 and in co-pending, commonly assigned U.S. patent application Ser. No. 07/662,536 filed by Gerald M. Weber et al. on Feb. 28, 1991, U.S. patent application Ser. No. 07/662,537 filed by Kenneth B. Buell et al. on Feb. 28, 1991, and U.S. patent application Ser. No. 07/662,543 filed by Gerald M. Weber et al. on Feb. 28, 1991 (collectively referred to herein as the "Ring Rolling" patent applications).

The fold lines in the corrugations of a ring rolled topsheet should run in the transverse direction so the topsheet is longitudinally extensible. In other embodiments, the fold lines could run in the longitudinal direction, both directions, and/or other directions. The topsheet 38 will be extensible in directions perpendicular to the fold lines.

In a preferred embodiment, the topsheet 38 is rendered hydrophilic so that liquids will transfer through the topsheet 38 faster. This will diminish the likelihood that body exudates will flow off the topsheet rather than being drawn through the topsheet and being absorbed by the absorbent core. The topsheet can be rendered hydrophilic by treating it with surfactants. Suitable methods of applying surfactants are described in U.S. Pat. Nos. 4,950,254 and 5,009,653 issued to Osborn.

In addition, in preferred embodiments, the inner surface 38B of topsheet 38 is secured in contacting relation with an underlying absorbent layer. This contacting relationship results in liquid penetrating topsheet 38 faster. The topsheet 38 may be kept in a contacting relationship with an underlying layer by bonding the topsheet to the underlying layer. However, it is not absolutely necessary to bond the face of the topsheet 38 to the face of the underlying layer. The topsheet 38 can be maintained in contact with an underlying absorbent component by applying adhesives between the topsheet and the underlying component, by entangling the fibers of the underlying layer with the topsheet, by fusing the topsheet 38 to an underlying absorbent layer by a plurality of discrete individual fusion bonds, or by any means known in the art.

B. The Absorbent Core

The absorbent core 42 is positioned between the topsheet 38 and the backsheet 40. The absorbent core 42 provides the means for absorbing menses and other body fluids.

The absorbent core 42 need not have an absorbent capacity much greater than the total amount of fluid anticipated to be absorbed. The absorbent core 42 is generally compressible, conformable, and non-irritating to the user's skin. It can comprise any material used in the art for such purpose. Non-limiting examples include natural materials such as comminuted wood pulp which is generally referred to as airfelt, creped cellulose wadding, hydrogel-forming polymer gelling agents, modified cross-linked cellulose fibers (such as those described in U.S. Pat. No. 5,217,445 issued to Young, et al. on Jun. 8, 1993, capillary channel fibers (that is, fibers having intra-fiber capillary channels such as those described in U.S. Pat. No. 5,200,248 issued to Thompson, et al. on Apr. 6, 1993), absorbent foams, absorbent sponges, synthetic staple fibers, polymeric fibers, peat moss, or any equivalent material or combinations of materials.

The polymeric gelling agents listed above may also be referred to as "absorbent gelling materials" or "superabsorbent materials". Polymeric gelling agents are those materials which, upon contact with liquids such as water or other body liquids, imbibe such liquids and thereby form hydrogels. In this manner, liquids discharged into the absorbent core 42 can be acquired and held by the polymeric gelling agent, thereby providing the articles herein with enhanced absorbent capacity and/or improved liquid retention performance. The polymeric gelling agent which is employed in the absorbent core 42 will generally comprise particles 41 of a substantially water-insoluble, slightly cross-linked, partially neutralized, hydrogel-forming polymer material. The polymeric gelling agent can be in many forms, including in the form of pellets, flakes, or fibers.

In one preferred embodiment shown in FIG. 2, the absorbent core 42 is a laminate. The laminate is comprised of a layer of superabsorbent polymer material, such as in the form of particles 41, disposed between two air-laid tissues, first and second tissue layers (or "upper" and "lower" tissue layers) 43 and 47, respectively. The first and second tissue layers 43 and 47 provide containment of the superabsorbent polymer material, improve lateral wicking of the absorbed exudates throughout the absorbent core 42 and provide a degree of absorbency. The tissue layers 43 and 47 can be comprised of a single tissue web which is folded with the superabsorbent material particles 41 between, or two separate sheets of the same (or different) tissue.

Figure 8:
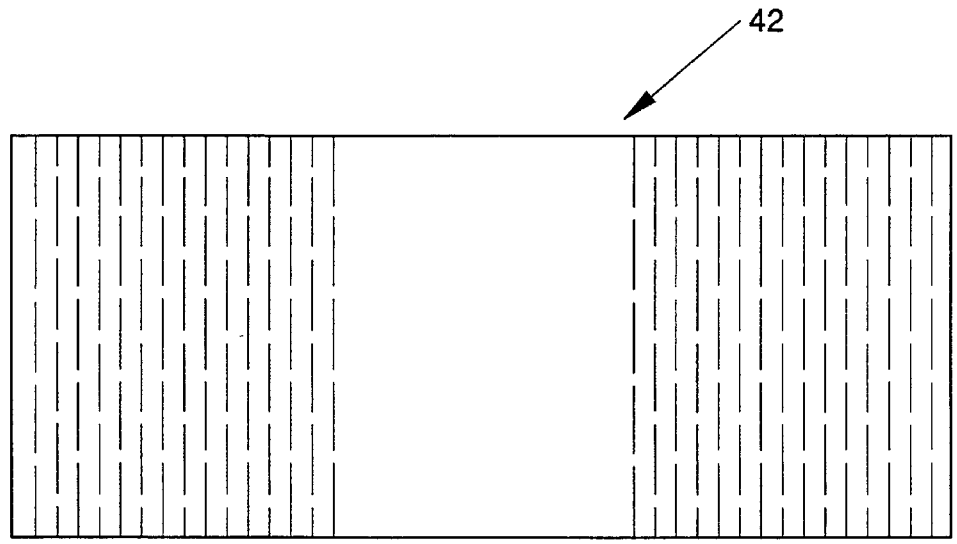
FIG. 8 is a plan view of an absorbent core that is provided with slits in the central region of the same.

A suitable laminate is a superabsorbent laminate known as WATER-LOCK L-535 available from the Grain Processing Corporation of Muscatine, Iowa (WATER-LOCK registered TM by Grain Processing Corporation). Such superabsorbent laminates are disclosed in U.S. Pat. No. 4,467,012, issued to Pedersen et al. on Aug. 21, 1984, U.S. Pat. No. 4,260,443, issued to Lindsay et al. on Apr. 7, 1981, and U.S. Pat. No. 4,578,068 issued to Kramer, et al. on Mar. 25, 1986. The laminate absorbent core 42 can be made extensible by cutting or slitting the same. FIG. 8 shows that the absorbent core 42 is a laminate as described above which is slitted or partially slitted for longitudinal extensibility.

In alternative embodiments, making the same from tissue paper having between 20% and 200% stretch (i.e., capable of extending to an extended dimension that is between about 1.2 and 3 times its unextended dimension). Such tissue sheets can be made by a number of processes. The tissue paper may in one embodiment, be conventionally creped tissue. For example, the tissue paper may be a BOUNTY tissue that is taken directly after it has been creped off of a Yankee dryer before any crepe is pulled out of the tissue. A process for making such a tissue is described in U.S. Pat. No. 5,098,522 issued to Smurkoski, et al. on Mar. 24, 1992.

In alternative embodiments, a tissue with no or very low initial crepe can be creped after lamination. The creping process in this case could occur by passing the laminate through two matched rolls such that they would yield a corrugated laminate tissue with stretch in the range of 20% to 200%. The corrugations should be perpendicular to the direction of desired stretch. In still other embodiments, the entire main body portion can be creped.

The longitudinal and end edges 22 and 24 of the main body portion 21 are preferably sealed to prevent the wicking and expulsion of liquid or liquid-containing superabsorbent material from the napkin when it is extended. Alternatively, the edges 42C and 42D of the absorbent core 42 may be sealed rather than sealing the edges of the entire main body portion. The edges of the core 42 may, for example, be wrapped or covered by a tissue layer. In other alternative embodiments, the edges of the tissue may be folded, or otherwise manipulated to prevent the wicking and expulsion of liquid or liquid-containing superabsorbent material particles 41 from the core 42. All permanent seals around the perimeter of the main body portion should not break upon lengthening (i.e., any seal is intended to remain for the duration of the use of the sanitary napkin.)

The absorbent core 42 may be made elastically extensible even though it has no elastic properties of its own. The absorbent core 42 can be made elastically extensible by attaching it to an elastic backsheet or topsheet so that the absorbent core 42 will extend and retract with the elastic topsheet or backsheet.

C. The Backsheet

The backsheet 40 prevents the exudates absorbed and contained in the absorbent core 42 from wetting articles which contact the sanitary napkin 20 such as pants, pajamas and undergarments. The backsheet 40 is impervious to liquids (e.g., menses and/or urine). The backsheet 40 is preferably manufactured from a thin plastic film, although other flexible liquid impervious materials may also be used.

The backsheet 40 may comprise a woven or nonwoven material, polymeric films such as thermoplastic films of polyethylene or polypropylene, or composite materials such as a film-coated nonwoven material. Preferably, the backsheet 40 is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Tredegar Film Products of Terre Haute, Ind., under the designation XP-39385.

The backsheet 40 is preferably embossed and/or matte finished to provide a more clothlike appearance. Further, the backsheet 40 may permit vapors to escape from the absorbent core 42 (i.e., the backsheet 40 may be breathable) while still preventing exudates from passing through the backsheet 40. Flushable or biodegradable backsheets can also be used, e.g., such as with the pantiliner devices described herein. Another suitable backsheet material is nonwoven/film laminate described in U.S. Pat. No. 5,007,906 issued to Osborn Apr. 16, 1991.

The backsheet 40 can be made extensible by performing a mechanical operation, such as pleating, corrugating, or ring rolling the backsheet material. Preferably, however, the backsheet 40 is made extensible by forming it from an elastomeric film such as the film described in U.S. Pat. No. 4,476,180 issued to Wnuk on Oct. 9, 1984. Such a film is obtained from Exxon Chemical Company of Lake Zurich, Ill. as Exxon film EXX-500 (formerly EXX-7).

Another particularly preferred extensible backsheet 40 is an extended adhesive film Formula #198-338 manufactured by the Findley Adhesives Company of Wauwatosa, Wisconsin. The Findley adhesive film is a fluid impervious film capable of extending 200–300%. The Findley adhesive film is preferred because it is also elastically extensible. At least one side of this film can be used with the adhesive "as is" in the sanitary napkin 20. For example, this side of the adhesive film can be adhered to the garment-facing side 42B of the absorbent core 42. The other side of the adhesive film that forms the garment-facing side 40B of the backsheet 40 may have its adhesive surface at least partially covered (or "blocked" to eliminate its adhesive characteristics). The adhesive defining the body-facing side 40A of the backsheet can also be at least partially blocked. The exposed adhesive can be blocked in a number of suitable ways. These include, but are not limited to attaching a layer of nonadhesive material to cover the exposed adhesive, and brushing or sprinkling a powdered material such as talcum powder or corn starch on at least part of the exposed adhesive. The partial blocking of the exposed adhesive on the garment-facing side 40B of the backsheet 40 can be used with the remaining exposed adhesive to create particular adhesive patterns for fastening the backsheet to the panty covering component.

In still other embodiments, an adhesive film can be created with one side that has adhesive tack, and one side without tack. One suitable adhesive film having these characteristics is a composite structure comprising a nonwoven elastomeric film with a low modulus pressure sensitive adhesive, such as adhesive film Formula #198-338 which is available with a blocking film such as film Formula H2301 from the Findley Adhesives Company. Such materials are further described (and used for other purposes) in U.S. Pat. No. 5,032,120 issued to Freeland, et al. on Jul. 16, 1991, and U.S. Pat. No. 5,037,416 issued to Allen, et al. on Aug. 6, 1991.

In other preferred embodiments, the backsheet 40 may comprise an extensible laminate structure comprised of two or more layers. The laminate can be comprised of layers which are each capable of different extensibility. For instance, a backsheet 40 can comprise a laminate formed of a layer of Findley adhesive film that is covered on one or both sides by an extensible nonwoven web or by an extensible film.

D. Combinations of TopSheet, Backsheet, and Core Materials and Assembly of the Same Into the Main Body Portion of the Sanitary Napkin.

The main body portion 21 of the sanitary napkin 20 of the present invention can be comprised of different combinations of the topsheet, backsheet, and core materials. The main body portion 21 may, as noted above, be comprised of all extensible components. The main body portion may also be comprised of any of the other types or combinations of extensible or inextensible topsheets, backsheets and absorbent cores that are described in PCT Publication Nos. WO 93/01785 and 93/01786.

The components of the main body portion described above (the topsheet, backsheet, and absorbent core) can be assembled in any suitable manner. In the preferred embodiment shown in FIGS. 1–3, the components of the main body portion are assembled in a "sandwich" configuration with the components sized so that the edges of the topsheet 38 and backsheet 40 extend outward beyond the edges of the absorbent core 42. The topsheet 38 and backsheet 40 are preferably at least partially peripherally joined using known techniques. As shown in FIG. 1, the topsheet 38 is preferably secured to backsheet 40 along a first seam, such as seam 90. Seam 90 is preferably liquid impervious. The seam 90 can be formed by any means commonly used in the art for this purpose such as by gluing, crimping, or heat-sealing.

The term "joined", as used herein, encompasses configurations in which an element is directly secured to another element by affixing the element directly to the other element; configurations in which the element is indirectly secured to the other element by affixing the element to intermediate memeber(s) which in turn are affixed to the other element; and configurations in which one element is integral with another element, i.e., one element is essentially part of the other element.

The components of the sanitary napkin 20 can be joined together by adhesives, stitching, heat and/or pressure bonds, dynamic mechanical bonds, ultrasonic bonds, intermingling or entanglement of the fibers or other structural elements comprising the components of the sanitary napkin, such as by meltblowing the fibers comprising one component onto another component, extruding one component onto another, or by any other means known in the art. Suitable means for attaching the components of the sanitary napkin are described in U.S. patent application Ser. No. 07/944,764 filed in the name of Cree, et al. on Sep. 14, 1992.

When the main body portion is comprised of extensible components, the components can be joined together in any suitable manner that allows the main body portion to extend. The backsheet 40, in one example comprises a stretchable adhesive film. The core 42 is placed on top of the backsheet 40. The topsheet 38 is then placed on top of the core 42. The portions of the edges of the topsheet 38 that extend outward beyond those of the core 38 are secured to those of the backsheet 40 using the adhesive around the perimeter of the backsheet film. It has been found that such a construction adequately secures the components of the sanitary napkin without further securing the faces of the adjacent components to each other. Although, as noted above, it is often preferred to secure some of the components at their faces, as well.

The above manners of joining the components are preferred for ease of construction. (Other means of uniting the various components can be used.) For instance, the present invention also includes so-called "tube" products. In these products, a liquid pervious cover material (such as topsheet material) can be wrapped completely around the absorbent core and the backsheet, and then the components can be secured together. In alternative arrangements, the topsheet could be wrapped around the core, and the wrapped core could be placed on and secured to the backsheet.

E. The Panty Covering Component.

The panty covering component 100 comprises a pair of side wrapping elements 52 that are disposed along the longitudinal side edges of the sanitary napkin to automatically wrap the sides of a wearer's panties. The panty covering component 100 provides an alternative to conventional side flaps.

FIGS. 1–5 show a preferred embodiment of the panty covering component. Before examining the features of the sanitary napkin shown in FIGS. 1–5 in greater detail, the functioning of the panty covering component, in its most basic forms, will be discussed with relation to FIGS. 9–15C.

Figure 9:
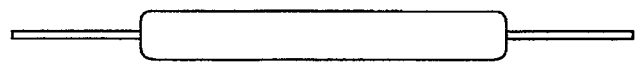
FIG. 9 is a simplified end view of a known sanitary napkin having longitudinally extensible flaps which, for simplicity, is shown with the flaps extended instead of being folded around the edges of a crotch of an undergarment as they normally would be during use.
Figure 9A:
FIG. 9A is a simplified end view of the sanitary napkin shown in FIG. 9 after the absorbent element has been compressed.

FIGS. 9 and 9A are simplified schematic end views of a sanitary napkin having longitudinally extensible flaps, such as the one described in U.S. Pat. No. 4,940,462 issued to Salerno. The sanitary napkin shown in the Salerno patent suffers from several drawbacks due to the fact that the longitudinally expandable flaps extend directly outward from the longitudinal sides of the absorbent element. The expandable flaps in Salerno are attached directly to an inextensible body. This limits the extensibility of the portions of the Salerno flaps that are located adjacent to the absorbent element. In order for the Salerno flaps to extend an amount sufficient to wrap around the panty elastics, particularly if the panty crotch stretches, the flaps have to have a relatively wide transverse dimension.

FIG. 9A also shows that any laterally inward compression of the absorbent portion of the Salerno sanitary napkin will cause the flaps to be pulled inward. This can result in a loss in the ability of the flaps to cover a given area of the wearer's panties (i.e., a loss in area coverage), and may also cause the flaps to become detached from the wearer's panties.

Figure 10:
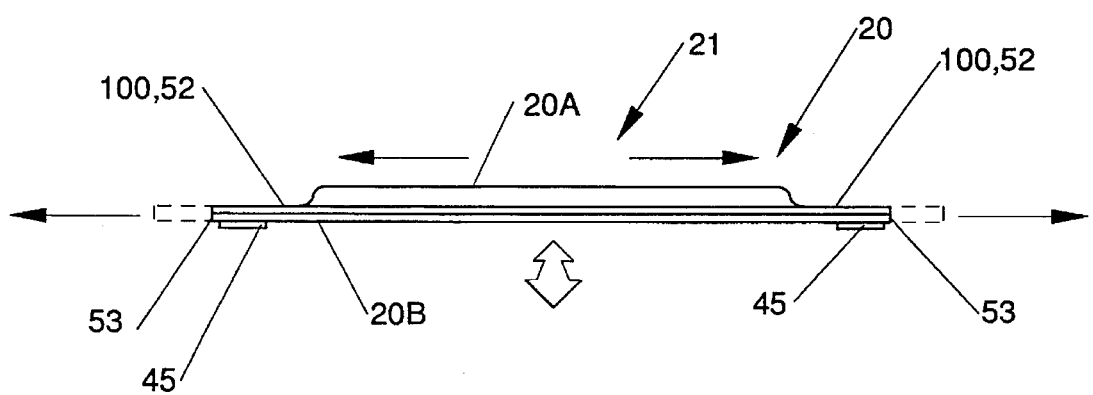
FIG. 10 is a simplified end view of an extensible sanitary napkin having extensible side wrapping elements.

FIG. 10 shows a first basic embodiment of the panty covering component of the present invention. The panty covering component 100 comprises side wrapping elements 52 that are extensible extensions from the longitudinal sides of an extensible sanitary napkin. The extensions are preferably extensions of non-absorbent components. The panty covering component (or the extensible portions thereof) can, in this, like most of the other embodiments described herein, be extensible in the longitudinal direction, the transverse direction, or both. When the panties are pulled up on the wearer's body, the stretching of the portions of the panties along the leg elastics causes the extensions to naturally fold around and wrap the elastic-containing edges of the panty crotch.

In this particular embodiment, the distal edges 53 of the extensions preferably extend from about ⅜ inch (about 1 cm) to about 2 inches (about 5 cm) from the edge of the absorbent core of the sanitary napkin. The extensible extensions can be comprised of one of the components of the main body portion, or they can comprise separate elements joined to the main body portion. In a particularly preferred version of this embodiment, an adhesive fastener 45 may be applied up to about ⅛ inch (3 mm) of the edge on the garment-facing side of the extensions to help hold the extensions in place around the panty crotch during vigorous motions by the wearer (although such fasteners are generally not required under normal circumstances).

Figure 26:
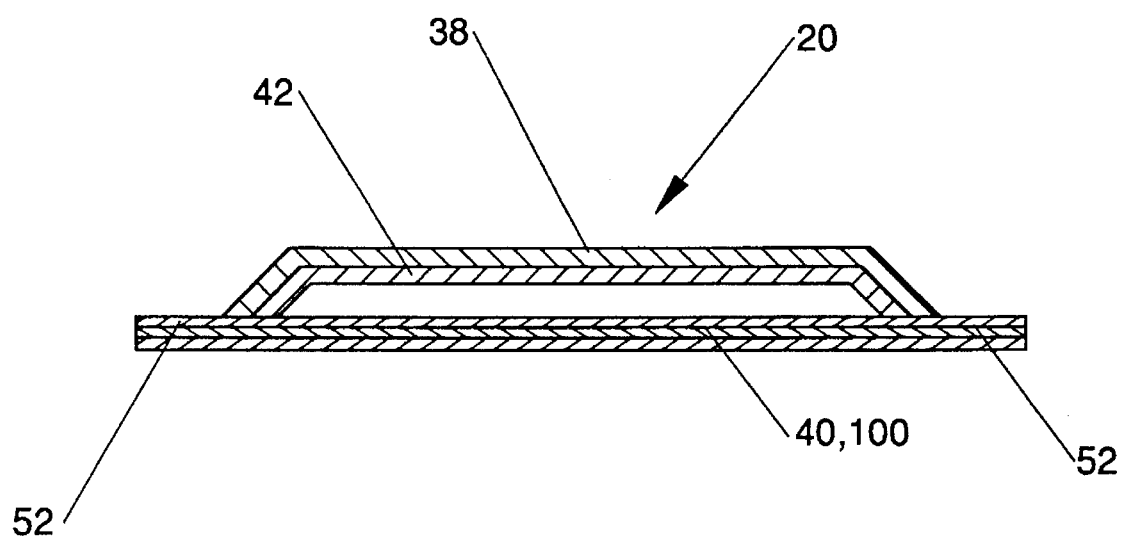
FIG. 26 is a simplified schematic cross-sectional view of a sanitary napkin comprised of extensible components in which the backsheet is an extensible material that extends outward beyond the topsheet and absorbent core to serve as the panty covering component.

In alternative versions of this embodiment, the extensions can be provided with regions that are permanently extensible (that is, regions that will have no tendency to retract after extension) along any of those portions of the extension that will be disposed in the area of the panty elastics. In other alternative versions, extensions can be folded, gathered, or pinched and sealed to further facilitate wrapping the elastic-containing edges of the panty crotch. FIG. 26 shows an alternative version of such an embodiment in which the sanitary napkin is extensible and the backsheet extends beyond the edges of the topsheet and absorbent core to form the extensible extensions. In this embodiment, all of the components of the sanitary napkin are preferably at least extensible in the longitudinal direction.

The fact that the sanitary napkin is extensible at least partially alleviates some of the problems associated with the Salerno sanitary napkin. The fact that the side wrapping elements are joined to an extensible body rather than to an inextensible body, allows the side wrapping elements to continue to stay wrapped around the sides of the panty crotch even if the panty crotch stretches.

It should be understood that the "basic" embodiments described herein are directed to certain features with which the panty covering component may be provided. These features can be combined in various different ways (or omitted from) the sanitary napkin of the present invention. That is, they are not all mandatory features.

Figure 11:
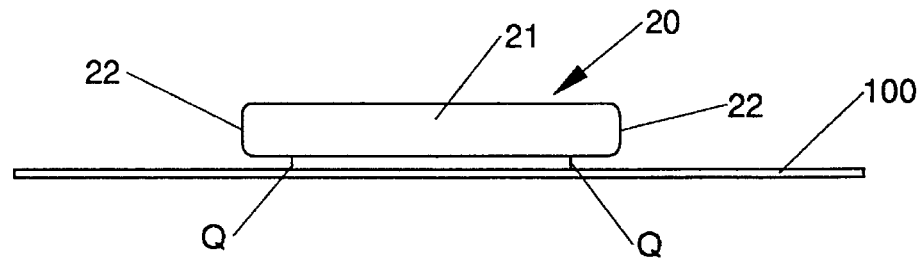
FIG. 11 is a simplified end view (similar to that of FIG. 9) showing a sanitary napkin having a panty covering component that is joined underneath the main body portion of the sanitary napkin at points of attachment that are inboard of the longitudinal edges of the main body portion.
Figure 11A:
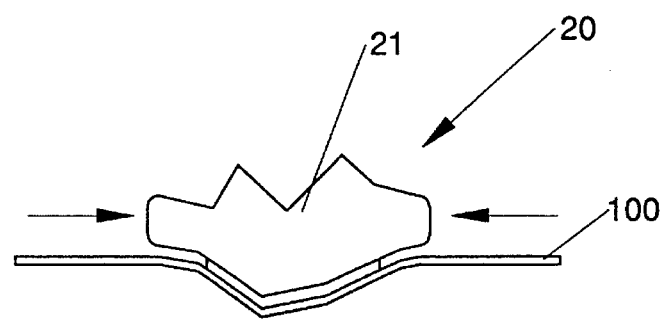
FIG. 11A is a simplified end view of the sanitary napkin shown in FIG. 11 after the absorbent element has been compressed.

FIGS. 11 and 11A show that in a second basic embodiment, the panty covering component 100 of the present invention is joined underneath to the main body portion 21 of the sanitary napkin inboard of the longitudinal side edges 22 of the main body portion. The panty covering component is otherwise unattached to the garment-facing side of the main body portion 21 of the sanitary napkin 20 between the points of attachment Q and the longitudinal side edges 22 of the main body portion. The embodiment shown in FIGS. 11 and 11A allows the panty covering component 100 to stretch between the points, Q, where the panty covering component is attached to the main body portion and the place where the panty elastics will cross the panty covering component. This allows the panty covering component to mold to and fold around the wearer's panty.

Figure 12:
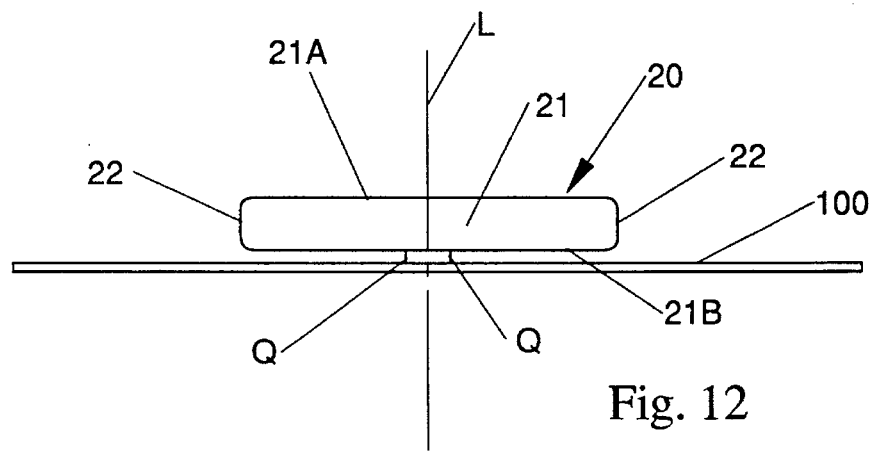
FIG. 12 is a simplified end view of a sanitary napkin similar to that of FIG. 11, only with the points of attachment being in the region of the longitudinal centerline of the sanitary napkin.
Figure 12A:
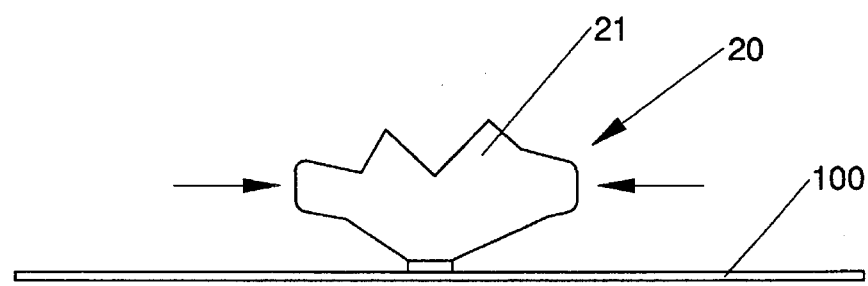
FIG. 12A is a simplified end view of the sanitary napkin shown in FIG. 12 after the absorbent element has been compressed.

FIGS. 12 and 12A show that in a third basic embodiment, the panty covering component can be joined a substantial distance inward of the longitudinal side edges 22 of the main body portion 21 of the sanitary napkin 20 so that the point of attachment is located in the region of the longitudinal centerline, L. The embodiment shown in FIG. 12 provides the advantage that it reduces the tendency for the compression of the main body portion (particularly compression of the absorbent core) to interfere with the operation of the panty covering component 100. The reduction in the tendency for the compression of the core to interfere with the operation of the panty covering component 100 occurs because the panty covering component 100 is not joined near the sides 22 of the main body portion. This prevents any forces exerted on the core from directly acting on the panty covering component. FIG. 12 shows that the absorbent core can be bunched inward to the points, Q, where the panty covering component 100 is attached to the main body portion without effecting the coverage of the panty covering component 100. This can be contrasted with FIG. 9A which shows how the flaps of the Salerno sanitary napkin will bunch inward in response to such forces.

Several additional matters should be noted with regard to the embodiment shown in FIG. 12. First, the location where the panty covering component 100 is joined to the garment side 21B of the main body portion 21 is most important in the central region 32 of the main body portion (or, if the main body portion is asymmetrical, the area of the main body portion that is intended to be between the wearer's legs) because this is primarily where any bunching of the main body portion 21 will occur. The central region 32 (shown in FIG. 1) is subject to bunching because this is in the area of the narrowest portion of the panty crotch and the narrowest space between the wearer's legs, when the wearer's legs are brought together. This is particularly true for the central about 3 inches (7.6 cm) to about 6 inches (15 cm) of the main body portion.

The second matter which should be noted with regard to the embodiment shown in FIG. 12 is that such an embodiment should preferably be provided with some type of stabilizing structure in order to prevent the main body portion 21 of the sanitary napkin 20 from pitching and rolling around the longitudinal centerline relative to the panty covering component 100.

The third matter which should be noted with regard to the embodiment shown in FIG. 12 is the manner in which the side wrapping elements function differently from the flaps of known sanitary napkins. For example, sanitary napkins are known which have flaps of various types attached inboard of the longitudinal sides of an absorbent component. Examples of such flaps are described in U.S. Pat. No. 4,589,876 issued to Van Tilburg and U.S. Pat. No. 4,900,320 issued to McCoy. The differences are particularly apparent with regard to the flaps of the sanitary napkin described in the McCoy patent. The flaps of the sanitary napkin described in the McCoy patent are intended to completely encircle the panty crotch and be affixed to each other. The flaps of the McCoy sanitary napkin are designed to gather the panty crotch inward. The side wrapping elements 52 of the sanitary napkin of the present invention do not overlap, nor are they designed to gather the wearer's panties. The side wrapping elements 52 are intended to adjust to the movements of the panties. That is, they move with the panties and allow the panties to move, rather than to constrain the movement of the panties as do the flaps of the McCoy sanitary napkin.

While attaching the panty covering component inboard of the longitudinal side edges of the main body portion is beneficial, additional benefits may be achieved by decoupling the main body portion from the panty covering component. The decoupling of the main body portion from the panty covering component refers to the ability of the main body portion to move away from the panty covering component in the z-direction. (For a discussion of the concept of decoupling in other contexts, reference can be made to U.S. Pat. No. 5,007,906 issued to Osborn, et al. on Apr. 16, 1991 and U.S. patent application Ser. No. 07/605,583 filed in the name of Visscher, et al. on Oct. 29, 1990.) The decoupling of the main body portion is achieved through a decoupling component (or "isolation component" or "intermediate component") 102 that is joined at points of juncture to the main body portion and at points of juncture to the panty covering component with extra material between the two sets of points. (The points of juncture may comprise lines, zones, etc., and, as a result, may be referred to simply as "junctures".)

Figure 13:
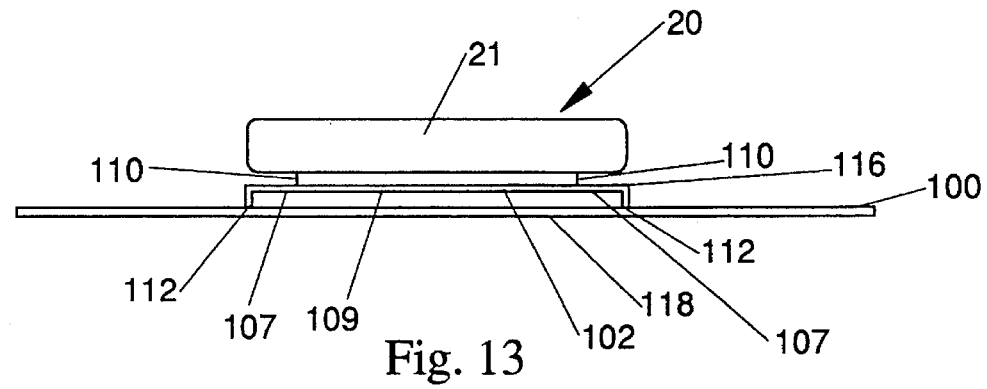
FIG. 13 is a simplified end view (similar to that of FIG. 11) showing of a sanitary napkin having a first type of structure which allows a portion of the main body portion of the sanitary napkin to decouple (or move apart) from the panty covering component.
Figure 13A:
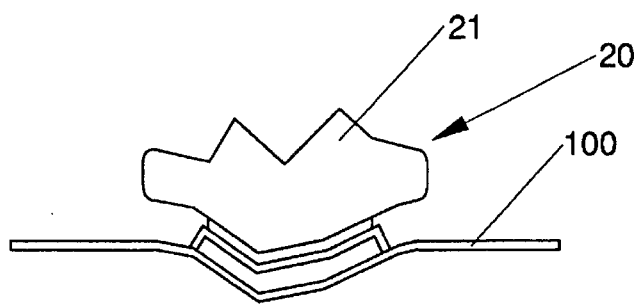
FIG. 13A is a simplified end view of the sanitary napkin shown in FIG. 13 after the absorbent element has been compressed.
Figure 14:
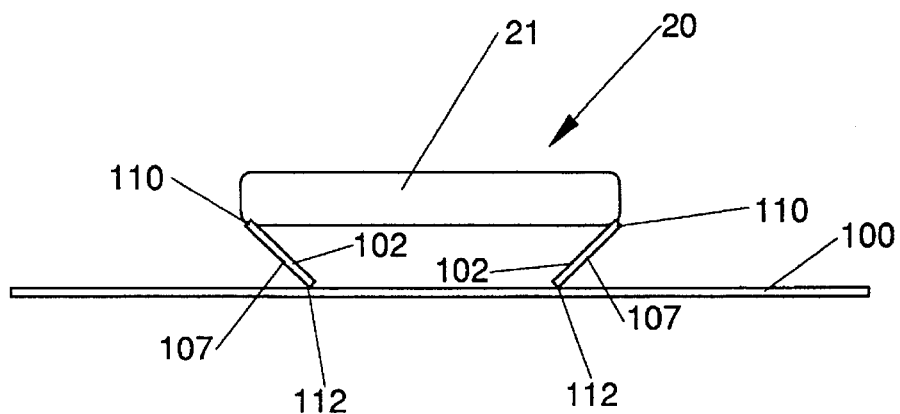
FIG. 14 is a simplified end view (similar to that of FIG. 11) showing of a sanitary napkin having a second type of structure which allows a portion of the main body portion of the sanitary napkin to decouple from the panty covering component.
Figure 14A:
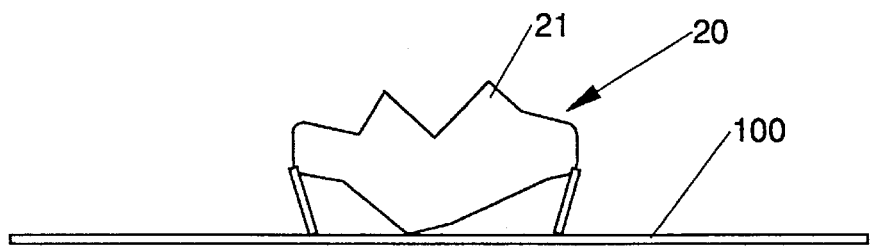
FIG. 14A is a simplified end view of the sanitary napkin shown in FIG. 14 after the absorbent element has been compressed.

Three basic examples of structures capable of decoupling are shown in FIGS. 13–15C (FIGS. 13 and 13A; FIGS. 14 and 14A; and FIGS. 15–15C). FIGS. 13–15C show that the extra material indirectly joins the panty covering component to the main body portion 21 of the sanitary napkin. The isolation component 102 is attached to the main body portion 21 at main body portion attachment points 110, and the isolation component 102 is attached to the panty covering component 100 at undergarment covering component attachment points 112. These three sets of figures show the various different possible relationships between the location of the main body portion attachments points and the undergarment covering component attachment points.

FIGS. 13 and 13A show a first example in which the sanitary napkin is provided with a construction that allows the main body portion 21 of the sanitary napkin to decouple from the panty covering component 100. A basic way of accomplishing this is for the decoupling component 102 to comprise a single piece of material or separate strips of material that form a pair of legs 107 that join the undergarment covering component 100 to the main body portion 102. The sanitary napkin shown in FIGS. 13 and 13A is characterized by the fact that the points of juncture 110 where the decoupling component 102 is joined to the main body portion 21 are inboard (i.e., closer to the longitudinal centerline) of the points where the decoupling component is joined to the panty covering component 100. The construction shown in FIG. 13A allows the main body portion 21 of the sanitary napkin to maintain close contact with the wearer's body and the panty covering component 100 to stay in the wearer's panties even when the panties move away from the wearer's body. The basic way of achieving the construction described above can be carried out in numerous different manners.

For example, in the embodiment shown in FIGS. 13 and 13A, the sanitary napkin 20 can be provided with a panty covering component 100 that is in the form of a two layer laminate structure, comprising an upper layer 106 and a lower layer 108. In this embodiment, the layers of the laminate are bonded at points of attachment 112 located toward the longitudinal sides of the laminate. The layers of the laminate are unbonded between the points of attachment. This allows the unbonded portion 109 of the upper layer 106 of the laminate (and the overlying main body portion 21 of the sanitary napkin) to separate from the lower layer 108 of the laminate and the panty crotch. The structure shown in FIGS. 13 and 13A provides the lateral stability needed to the embodiment shown in FIG. 12. In addition, the upper layer can be provided with transverse extensibility to reduce the tendency for the compression of the core to pull the sides of the panty covering component inward.

While the construction of the sanitary napkin is shown in FIG. 13 is suitable for allowing the main body portion to decouple from the panty covering component, as shown in FIG. 13A, a degree of bunching of the main body portion could still lead to some tendency for the side wrapping elements to be pulled inward. The embodiment shown in FIGS. 13 and 13A, however, is still believed to represent an improvement over the Salerno sanitary napkin in this regard.

Figure 25:
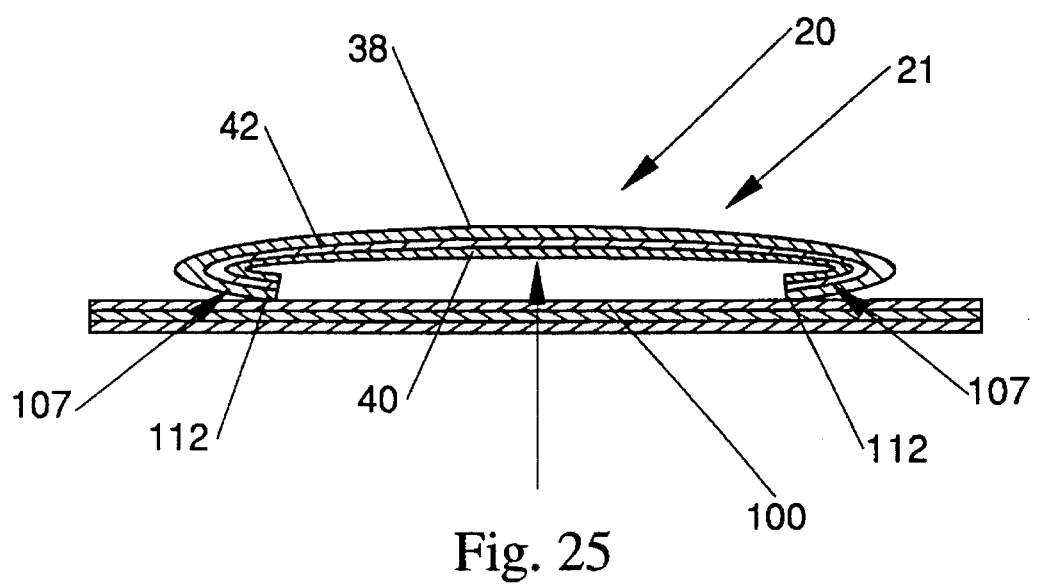
FIG. 25 is a schematic cross-sectional view of a sanitary napkin having its longitudinal side margins folded underneath its main body portion and attached to a panty covering component.

FIGS. 14 and 14A show a second example of a decoupling feature. In this second example, the sanitary napkin 20 is provided with extra material in the form of a pair of inwardly attached legs 107 that join the panty covering component 100 to the main body portion 21. (That is, the points where the decoupling component are joined to the main body portion are outboard of the points where the decoupling component is joined to the panty covering component.) The inwardly attached legs may comprise a number of possible types of structures. For instance, as shown in FIG. 25, the inwardly attached legs can comprise a portion of one or more of the components of the sanitary napkin which is/are pleated and folded under the main body portion of the sanitary napkin and attached to the panty covering component. Alternatively, the inwardly attached legs can comprise separate elements that are connected to the main body portion of the sanitary napkin and the panty covering component. The embodiment shown in FIGS. 14 and 14A provide the advantage that the panty covering component is not subject to being pulled inward by compression of the core and the legs provided the main body portion with stability from pitching and rolling relative to the main body portion.

Figure 15:
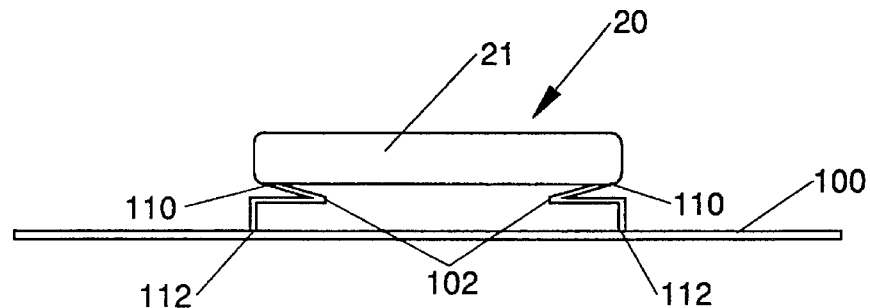
FIG. 15 is a simplified end view (similar to that of FIG. 11) showing of a sanitary napkin having a third type of structure which allows a portion of the main body portion of the sanitary napkin to decouple from the panty covering component.
Figure 15A:
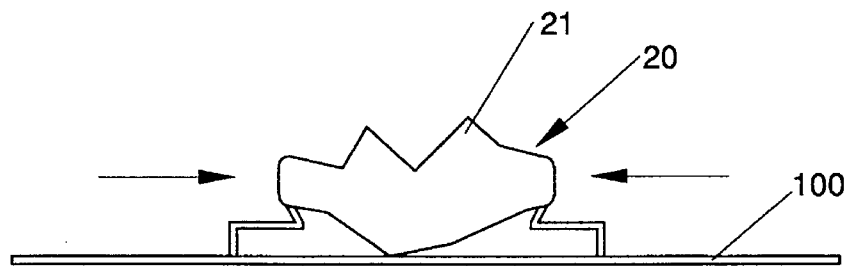
FIG. 15A is a simplified end view of the sanitary napkin shown in FIG. 15 after the absorbent element has been compressed.
Figure 15B:
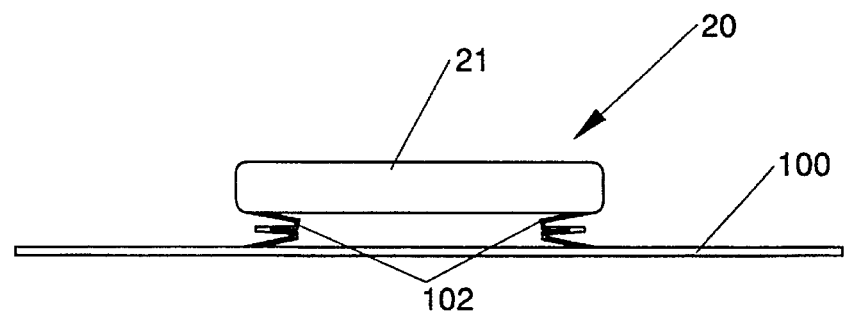
FIG. 15B is a simplified end view of a sanitary napkin having flaccid material that joins the main body portion of the sanitary napkin to the panty covering component which allows a portion of the main body portion of the sanitary napkin to decouple from the panty coveting component.
Figure 15C:
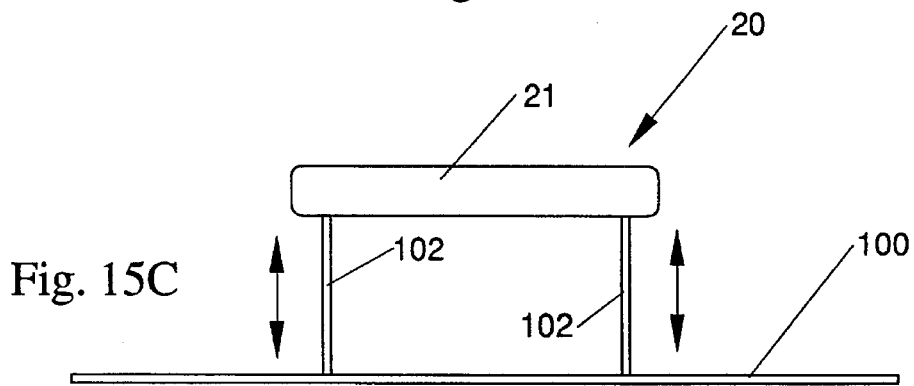
FIG. 15C is a simplified end view of a sanitary napkin having extensible material that joins the main body portion of the sanitary napkin to the panty covering component which allows a portion of the main body portion of the sanitary napkin to decouple from the panty covering component.
Figure 16:
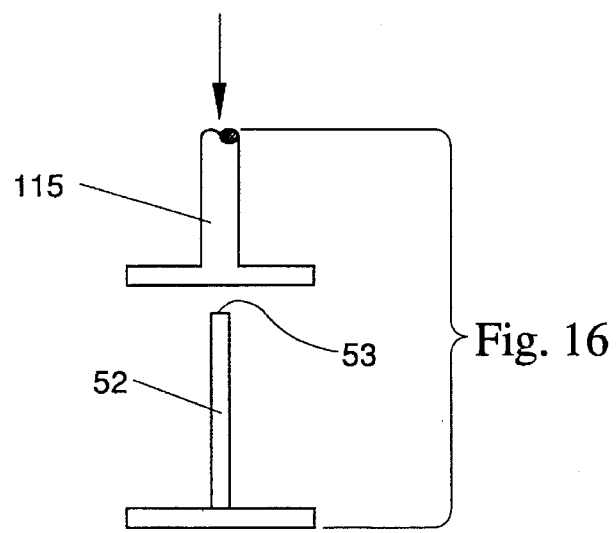
FIG. 16 is a simplified schematic side view of the procedure used to measure resistance to edge compression of the side wrapping elements.

FIGS. 15 through 15C show a third example in which a sanitary napkin is provided with a construction that allows the main body portion of the sanitary napkin to decouple from the panty covering component. The panty covering component shown in FIGS. 15 and 15A has pleated slack material between the main body portion and the panty covering component. This sanitary napkin combines the features of the embodiments shown in FIGS. 13 and 14. This panty covering component can be thought of as having legs with a lower portion like that shown in FIG. 13 and an upper portion like that shown in FIG. 14. The lower portion of the connecting structure between the main body portion 21 and the panty covering component 100 helps prevent the compression of the main body portion 21 from interfering with the molding of the panty covering component 100 to the wearer's panties. The upper portion of the connecting structure allows the main body portion to be bunched or molded to the wearer's body (e.g., to assume a "W"-shape) without causing the panty covering component 100 to be pulled inward resulting in losing coverage of the panty covering component.

FIGS. 15B and C show two additional versions of the type of extra material that joins the main body portion to the panty covering component. FIG. 15B shows a version having material in the form of flaccid (or slack) material joining the main body portion to the panty covering component. FIG. 15C shows a version having extensible material between the main body portion and the panty covering component.

The panty covering component features shown in FIGS. 15 through 15C are particularly desirable for products having thicker (e.g., greater than about 8 mm thick) main body portions. When the sides of the main body portion of the sanitary napkin are not constrained as they are in FIG. 14, they are able to move to fit up close to the wearer's body.

The decoupling component 102 has been described above in terms of how it can interact to allow the main body portion 21 of the sanitary napkin to separate from the panty covering component in the z-direction. The decoupling component can also enhance the functioning of embodiments in which the panty covering component is joined to an inextensible main body portion. In these cases, the decoupling component is preferably provided with extensibility under the same or lesser forces than those that cause the panty covering component to extend. The decoupling component is, thus, able to serve as a stretch isolation component (or "isolation component") to allow the panty covering component 100 to extend more independently of the inextensible (or less extensible) components of the main body portion.

With the fundamental concepts and structures of the panty covering component described above in mind, the preferred embodiment shown in FIGS. 1–5 will now be discussed in greater detail. The sanitary napkin shown in FIGS. 1–5 comprises a panty covering component that comprises at least one sheet of extensible material 100 which is used in conjunction with an isolation element 102.

The sheet of extensible material 100 shown in FIGS. 1–5 comprises a racetrack-shaped sheet of material that is larger in dimensions than the main body portion of the sanitary napkin. The panty covering component 100 may be of any suitable size and shape. For example, the panty covering component 100 may have certain dimensions that are less than or equal to those of the main body portion of the sanitary napkin. The panty covering component may be oval, rectangular, irregular, or some other suitable shape.

FIG. 1 shows that portions of the sheet of extensible material 100 extend laterally outward beyond portions of the longitudinal edges 22 of the main body portion 21 of the sanitary napkin 20 in the central region 32 of the sanitary napkin 20. The portions of the sheet of extensible material 100 that extend laterally outward beyond the longitudinal edges 22 of the sanitary napkin 20 in the central region 32 provide side wrapping elements 52 that can be folded around the edges of the wearer's panties.

It should be understood, however, that while the panty covering component 100 is shown as being a single sheet of material having portions which define the side wrapping elements 52, other embodiments are also within the scope of the present invention. For instance, in alternative embodiments, the side wrapping elements 52 may each comprise one or more separate pieces attached to the main body portion 21 of the sanitary napkin. In still other alternative embodiments, the side wrapping elements 52 may be integral portions of one or more components of the main body portion. In addition, while the side wrapping elements 52 are shown as extending from each longitudinal edge of the main body portion, there may only be one side wrapping element extending from one of the edges of the main body portion. Further, the side wrapping elements are preferably mirror images of each other, and are symmetrical about the longitudinal centerline. However, it should be understood that the shape and location of the side wrapping elements described herein are those of a preferred embodiment, and other embodiments are also possible. For instance, the side wrapping elements 52 may be offset along the longitudinal centerline more towards one end edge of the main body portion than the other.

In the embodiment shown in FIGS. 1–5, the sheet of extensible material 100 is preferably at least extensible in the longitudinal direction. The sheet of extensible material 100 (or any of the other panty covering components or components of the sanitary napkin described herein) can, however, be extensible only in the transverse direction, or extensible only in a direction between the longitudinal and transverse directions, or be provided with bi-directional, or multi-directional extensibility.

The sheet of extensible material 100 can be made of any suitable material. In one non-limiting example, the sheet of extensible material 100 comprises a laminate. The laminate comprises a sheet of extensible film such as Findley Adhesive 198–338 secured between two longitudinally extensible nonwoven webs. In another embodiment, the sheet of extensible material 100 can comprise an adhesive film secured between extensible nonwoven webs or between ring rolled plastic film sheets such as those of a type that can be used for the backsheet.

The side wrapping elements 52 are smaller than conventional flaps. (That is, the side wrapping elements do not have as great a span from distal edge to distal edge.) Preferably, the size of the side wrapping elements relates to the size of the crotch region of the wearer's panties. Panties have crotch widths that average about 65–70 mm (about 2¾ inches) measured at the narrowest point of the crotch. Panties come in a wide variety of sizes, however. The width of panty crotches can range from about 2 inches (about 5 cm) to about 4½ inches (about 11.4 cm). The smallest span of conventional flaps is believed to be about 5 inches (about 12.7 cm) for small tab-like flaps that are on some current products.

With these factors in mind, the width of the side wrapping elements should not be large enough to overlap when they fold under the wearer's panties. The dimensions of the side wrapping elements can be expressed in terms related to the boundaries of main body portion of the sanitary napkin. For instance, the span of the side wrapping elements 52 can be expressed in terms of the perpendicular distance in the x-y plane, $D_1$, from the most inward point on the longitudinal side edge of the main body portion (i.e., the point closest to the longitudinal centerline) R to the distal edge 53 of the side wrapping elements 52. The side wrapping elements 52 preferably extend a distance that is less than or equal to about 1¼ inch (about 3 cm) from the most inward portion of the main body portion of the sanitary napkin. More preferably, the side wrapping elements extend less than or equal to the following distances from the most inward point on the main body portion: about 1 inch (about 2.5 cm), about ¾ inch (about 2 cm), about 1.5 cm, and about 0.5 inch (about 1.25 cm).

The span of the side wrapping elements 52 can alternatively be specified in absolute terms of the distance from the distal edge to distal edge when the side wrapping elements 52 are extended laterally in opposite directions. Expressed in this manner, the span of the side wrapping elements from one distal edge to the other (and, thus also the span of the panty covering component) is preferably less than about 5 inches (about 12.7 cm) more preferably less than or equal to about 4¾ inches (about 12 cm). The minimum span of the side wrapping elements should be greater than or equal to any of the following amounts provided the span is also greater than the width of the panty crotch: about 2½ inches (about 6.4 cm); about 3 inches (about 7.6 or 8 cm); or about 3½ inches (about 9 cm). A preferred range for the span of the side wrapping elements is between about 3½ inches to about 4¾ inches. Even more preferably, the side wrapping elements have a span of between about 4 inches (about 10 cm) to about 4½ inches (about 11.5 cm).

The side wrapping elements 52 can have a length (longitudinal dimension) that varies within a large range. The length of the side wrapping elements 52 is preferably at least as large as the longitudinal dimension of known types of flaps (such as those described in the Background of the Invention) that attach to each other or to the underside of a wearer's panties. The side wrapping elements, therefore, can extend primarily from the central region of the main body portion of the sanitary napkin. Alternatively, the side wrapping elements can have a length that is as long as, or longer than, the length of the main body portion. Providing the sanitary napkin with side wrapping elements that are shorter than the length of the main body portion, however, may be preferred from a cost standpoint since such a sanitary napkin will require less material to make.

The panty covering component 100 should have additional features in order to automatically wrap the edges of the wearer's panties and stay in place around the same. For example, at least portions of the sheet of extensible material 100 preferably comprise a material having a low return force and a high set. These are materials that, when stretched, will not tend to return all the way to their unstretched dimensions. They will tend to remain (or set) close to their extended dimensions.

When the side wrapping elements 52 comprise a material having a high set, they will stretch to fit around the crotch of the wearer's panties. The high set reduces the tendency of the side wrapping elements 52 to retract and bunch the wearer's panties, or to unfold from the underneath the panties.

The term "set", as used herein, refers to the amount of permanent deformation (as a percentage of the original sample length) remaining in a sample after application and removal of the indicated strain. The procedure and equipment are described in the following. (Unless otherwise specified, all tests described herein are performed on samples that have been conditioned by leaving them in a room at 50% relative humidity and at 73° F. for a period of two hours prior to the tests.)

Figure 27:
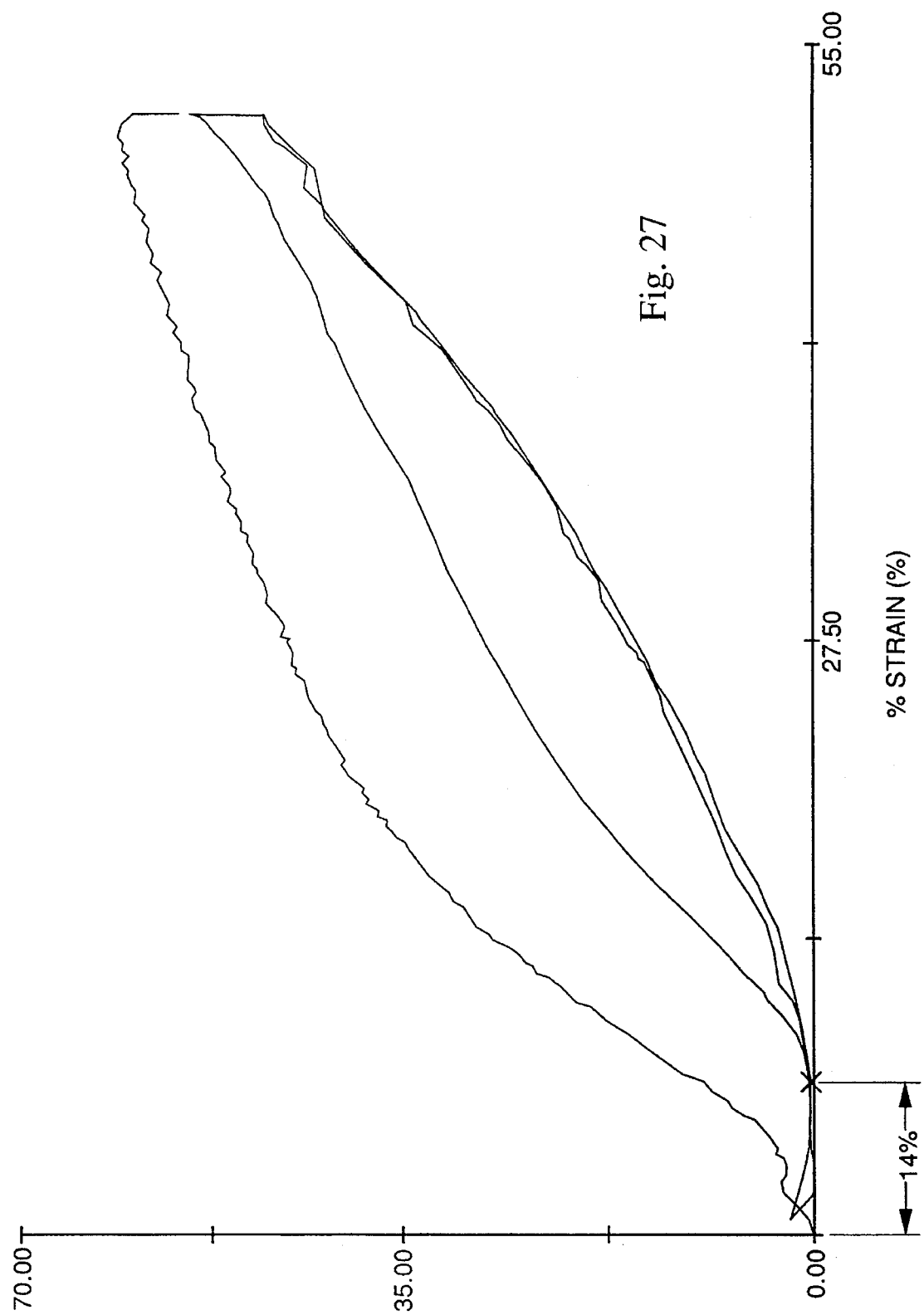
FIG. 27 is a graph showing the "set" of an extensible material after going through several cycles of elongation.

The set of a material is determined by pulling a 1" wide ×4" long (2.5 cm×10 cm) sample of the material to a given strain in an Instron model testing apparatus 1122, using a crosshead speed of 10 in/min. (25 cm/min.). The sample is mounted in the Instron grips so that the axis of elongation is parallel to the long dimension of the sample. The gage length of the sample (distance between gripping points is 2" {5 cm}). The strain used for this particular test is 30% (i.e., a 2" {5 cm} sample is pulled to 2.6" {6.6 cm}) and is held for thirty seconds at that strain. The separation between the grips is then returned to 2" (0% strain on the sample) and held at this position for 60 seconds. This cycle is then repeated. The percent set is determined as the first point on the strain axis where the force to elongate is greater than zero during the second cycle. This is illustrated in FIG. 27. An average percent set for three samples is reported. The material comprising the extensible material preferably has a set greater than or equal to 10% strain and more preferably has a set greater than or equal to 15%, 20%, 25%, or 30% strain (at 30% set all deformation is permanent).

Materials having a high set are particularly useful in several selected portions of the sanitary napkin. Two such portions are the regions of the fold lines where the side wrapping elements 52 are folded around the curved leg openings in the crotch of a pair of panties. The material in these areas is stretched when the side wrapping elements 52 are folded around the crotch of the panties. The stretching also puts tension on the material, outward of the fold lines along the distal edges of the side wrapping elements 52. (The effect of such stresses on components of a sanitary napkin with conventional flaps is described in greater detail in U.S. Pat. No. 4,917,697 issued to Osborn, et al. on Apr. 17, 1990.)

Examples of materials having a high set are zero strain nonwoven materials, such as a ring rolled nonwoven material or a nonwoven web comprised of unbonded fibers. In one embodiment, the entire sheet of extensible material 100 could comprise one of these types of materials. In other embodiments, the sheet of extensible material 100 could only have side wrapping elements 52 comprised of such materials. In such a case, the entire sheet of extensible material 100, with the exception of the side wrapping elements 52, could be comprised of the laminate with an extensible adhesive film therein. The extensible adhesive film, in such an embodiment, preferably omitted from the portion of the sheet comprising the side wrapping elements 52. The sheet of extensible material 100 that has the extensible adhesive therein will be elastically extensible. The side wrapping elements 52, however, will not be elastically extensible. The side wrapping elements 52 can, as a result, be folded around and attached to the underside of the wearer's panties and will not tend to flip back.

In other embodiments, only portions of the side wrapping elements 52 could comprise materials having a high set. For instance, the portions of the side wrapping elements 52 located on and near the axes where the side wrapping elements 52 are folded around the panty crotch may be comprised of such materials, while the remaining portions of the side wrapping elements 52 are not to relieve the stresses where they are concentrated when the side wrapping elements are folded under the panties.

The side wrapping elements 52 preferably also have several properties which allow them to wrap the sides of the wearer's panties and stay folded around the panty elastics without unfolding. These properties are low return force, resistance to edge compression and fold retention.

Return force is measured as follows: A 1"×4" long (2.5 cm×10 cm) sample is cut from the material to be tested so that the long axis of the sample is in the direction of lowest modulus (highest extensibility at lowest force) of the material. The sample is then mounted in a fixture comprising a force gauge, a steel rule for measuring extension of the sample and two clamps to hold the sample separated by a distance of 2" (5 cm) (the gage length). One of the clamps is attached to the force gauge and the other is attached to a lab jack which can be raised and lowered. The entire apparatus is placed in an oven set at a temperature of 98° F. (37° C.), and the sample is clamped between the two grips. The sample is pulled to 30% strain (2.6" e.g. 6.6 cm) and held at this position for 5 minutes. The strain on the sample is then reduced to 25% and the force on the force gage is reported as the return force at 25%. This is to simulate the temperatures and strains placed on a material during wearing of the product. The average return force of three samples is reported. The return force should be less than or equal to about 100 grams, preferably less than or equal to about 50 grams, and most preferably less than or equal to about 25 grams.

The "resistance to edge compression" refers to the measurement of how substantial the material is that comprises the side wrapping elements. Specifically, edge compression refers to the tendency of the material comprising the side wrapping elements 52 to buckle when the side wrapping elements are extended to form a planar extension and forces are applied perpendicular to the plane of the side wrapping elements. The resistance to edge compression can be measured by placing a plate or block 115 perpendicular to the distal edge 53 of the side wrapping element 52 and applying a force with the block perpendicular to the plane of the side wrapping elements. This property is important because if the material comprising the side wrapping elements is insubstantial, it will bunch up when forces are applied by the wearer's panty elastics to the side wrapping elements during wear. The side wrapping elements preferably have a resistance to edge compression of greater than or equal to about 5 grams, more preferably greater than or equal to the following amounts: about 7 grams; about 10 grams, and about 15 grams.

The edge compression test uses the Instron Model 1122 equipped with a compression load cell which is interfaced with Testworks™ software made by Sintech, Inc., and run on a Gateway 486/33 Hz computer. All of the parameters for testing are specified in the computer program, for example the crosshead speed, the strain up and the strain down. Also, all the data collection, data analysis and graphing are done by Testworks.

Figure 28:
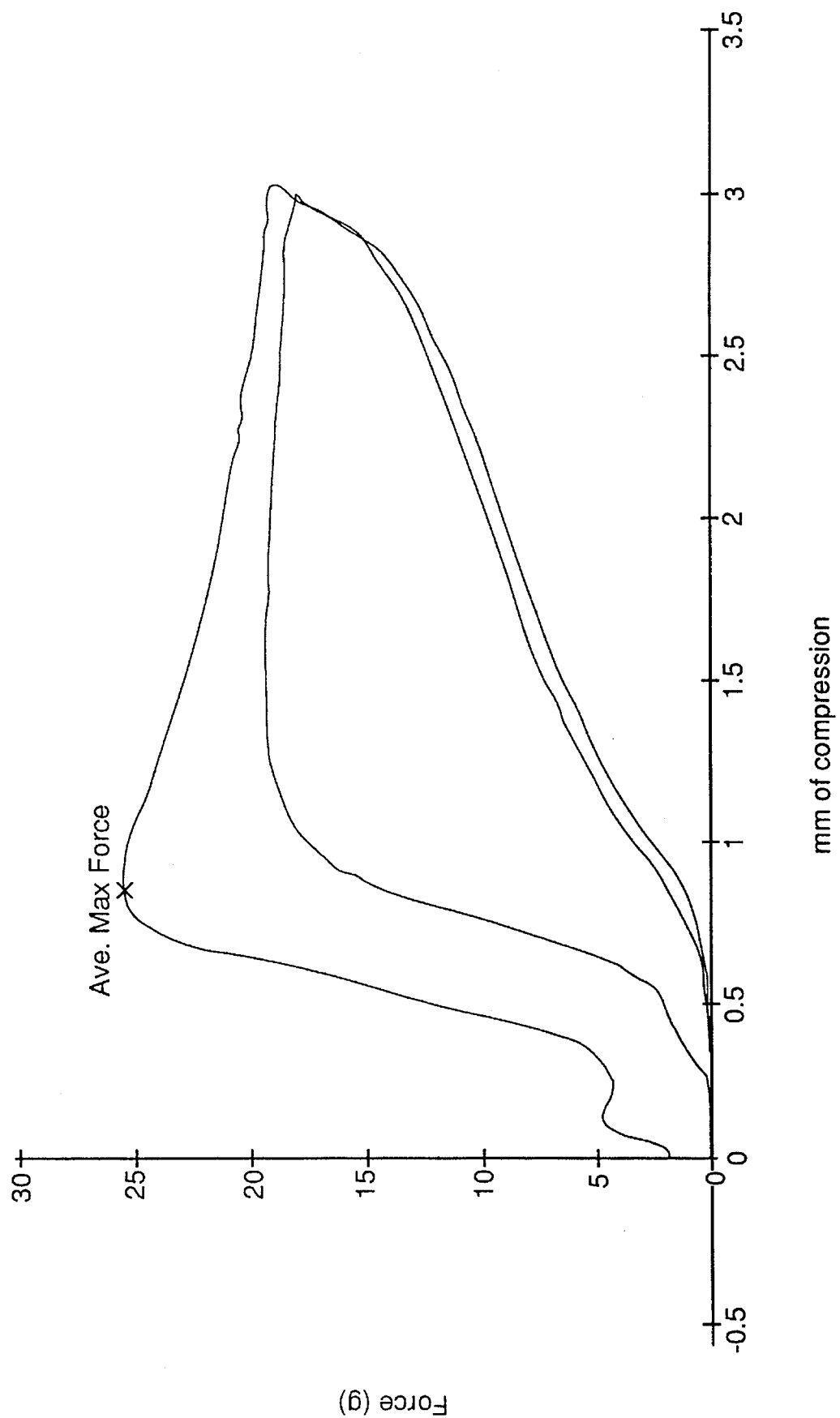
FIG. 28 is a graph that shows the edge compression of an extensible material.

A 9 mm by 25 mm sample is cut from the panty covering component so that the distal edge 53 of the side wrapping element is parallel to the 25 mm long edge of the sample. The sample is glued on its long edge in an upright position to a glass slide (i.e., perpendicular to the face of the slide). The glass slide is called the sample holder. The sample and holder are placed on a platform on top of the crosshead. The crosshead speed is set for 10 in/min (25 cm/min). A T-bar is attached to the compression cell and the crosshead is raised until a load of 0.5 grams is placed on the sample. The gage length is set to zero at this point and the crosshead continues to move up to a distance of 3 mm. The crosshead then returns to zero extension and the cycle is repeated. The maximum force of the two cycles is recorded and the average of five samples is reported as the Edge Compression Force. This is shown in FIG. 28.

The "fold retention" refers to the ability of the side wrapping elements to stay in place after they have been folded around a panty crotch. Fold retention is measured by the following procedure. A side wrapping element is first folded around a panty crotch. The folded side wrapping element is then placed folded side upward on a flat surface. A 105 gram weight is placed on the side wrapping element for a period of 5 minutes. Also, this test is run at 98° F. The weight is removed, and the side wrapping element is allowed to unfold (if there is any tendency for it to do so). The amount, if any, the side wrapping element has unfolded is measured by measuring the angle formed between the side wrapping element and the flat surface after 30 seconds following the removal of the weight. The smaller the angle the side wrapping element makes with the flat surface, the better fold retention the side wrapping element has. The side wrapping elements preferably have a fold retention measured in the foregoing manner of less than or equal to about 90°, and more preferably, less than or equal to about 45°, and most preferably less than or equal to about 20°.

In a particularly preferred embodiment, the side wrapping elements can be at least partially comprised of a material, with a "dead fold" property such as aluminum foil or SARAN wrap so the side wrapping elements will have very little tendency to unfold after being folded.

The panty covering component 100 in the preferred embodiment shown in FIGS. 1–5 is used with an isolation element 102. The isolation element 102 provides the sanitary napkin with slack material between the main body portion 21 and the panty covering component. This allows the panty covering component 100 to decouple so the main body portion may move closer to the body when panties pull away from the body.

The isolation element 102 can also be used to connect the sheet of extensible material 100 to an inextensible component of the main body portion of the sanitary napkin (or to a component that is less extensible than the sheet of extensible material 100). This is important when it is desired to create a sanitary napkin that stretches with the wearer's panties when one or more of the components of the main body portion are either relatively inextensible or less extensible than the wearer's panties. If the isolation element 102 serves this purpose, the isolation element can comprise any suitable type of component that allows the sheet of extensible material 100 to extend more independently of the less extensible components than if such an element were not present. The isolation element, thus, can be said to "isolate", "disassociate", or "decouple" the extensibility of the sheet of extensible material 100 from the inextensible components of the sanitary napkin.

FIGS. 1–5 show an embodiment in which the isolation element 102 is in the position of the backsheet 40 of the sanitary napkin 20. The isolation element 102 shown in FIGS. 1–5 preferably comprises a nonwoven web that is extensible at least in the longitudinal direction. The main body portion of the embodiment shown in FIGS. 1–5 has a liquid impervious barrier between the absorbent core and the isolation component. The isolation element can, however, replace the backsheet in other embodiments. In other embodiments, the sanitary napkin 20 may have a conventional backsheet, and the isolation element 102 may comprise a separate component that is attached to the backsheet 40. The isolation element 102 may be liquid pervious if it is used in addition to a backsheet. The isolation element 102 is preferably liquid impervious if it replaces the backsheet.

The panty covering component (or sheet of extensible material 100 in FIGS. 1–5) should, as discussed above, preferably be joined to the main body portion 21 of the sanitary napkin (or in the case of the embodiment shown in FIGS. 1–5, to the isolation element 102) at certain discrete points). The sheet of extensible material 100 can be joined to the the isolation element 102 by any suitable attachment mechanism. Suitable attachment mechanisms include, but are not limited to adhesives, and the like.

FIG. 1 shows one way the sheet of extensible material 100 may be attached to the isolation element 102. The attachment mechanism 108 comprises a large zone of adhesive 104 disposed along a portion of the longitudinal centerline L, and smaller adhesive areas 106 in the corners 27 of the sanitary napkin 20. These adhesives can be extensible or inextensible. The large zone of adhesive 104 can comprise adhesive in any suitable pattern. The large zone of adhesive 104 can comprise one or more strips, patches, spots, or lines of adhesive. The strips (or the like) of adhesive within the large zone 104 can be intermittent or continuous. The length and width of the large zone of adhesive 104 can range in size. The length of the large zone of adhesive 104 can range in size from a small patch located along the transverse centerline T to a zone that extends nearly the length of the sanitary napkin. The large zone of adhesive in the embodiment shown is about 6 inches (about 15 cm.) long. The large zone of adhesive 104 can range from very narrow to fairly wide. The width of the large zone of adhesive 104 can be so small that it is just a thin line of adhesive disposed along the longitudinal centerline. The following discussion describes some of the factors involved in choosing the configuration of the attachment mechanism, such as the large zone of adhesive 104 and smaller adhesive areas 106.

Figure 17:
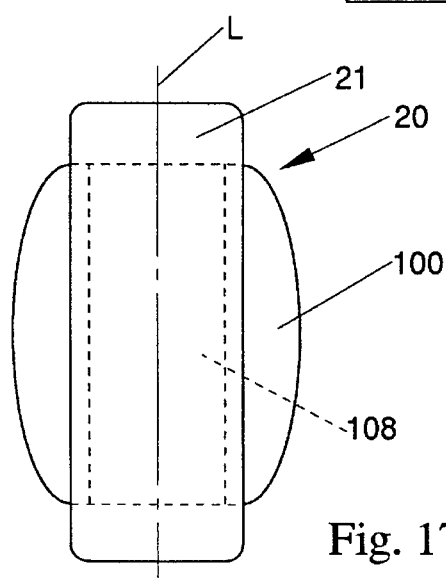
FIG. 17 is a plan view of a sanitary napkin having an attachment mechanism used to join the panty covering component to the main body portion of the sanitary napkin that comprises a rectangular zone that is centered about the longitudinal centerline.
Figure 18:
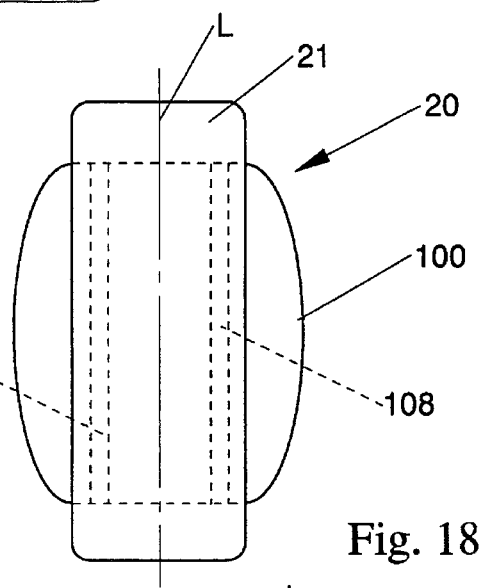
FIG. 18 is a plan view of a sanitary napkin having an attachment mechanism used to join the panty covering component to the main body portion of the sanitary napkin that comprises two strips that are oriented in the longitudinal direction.

There are many possible alternative configurations of attachments between the panty covering component and the main body portion of the sanitary napkin. Several configurations for the attachment mechanism are shown in FIGS. 17–20. (FIGS. 17–20 also show several examples of panty covering components that are shorter in the longitudinal dimension than the main body portion of the sanitary napkin.) FIG. 17 shows an attachment mechanism 108 that is in the form of a rectangular zone or block that is centered about the longitudinal centerline. FIG. 18 shows an attachment mechanism 108 that is in the form of two strips that extend in the longitudinal direction. The strips are on opposite sides of the longitudinal centerline. The strips can be in any suitable configuration that extends generally in the longitudinal direction. Suitable configurations include, but are not limited to linear strips, curvilinear strips, intermittent strips, and the like. The strips are located near, but inward from the longitudinal side edges 22 of the main body portion 21.

Figure 19:
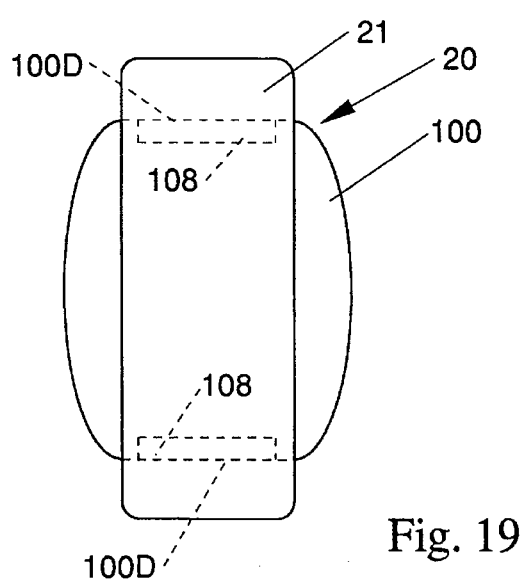
FIG. 19 is a plan view of a sanitary napkin having an attachment mechanism used to join the panty covering component to the main body portion of the sanitary napkin that comprises two strips that are oriented in the transverse direction.
Figure 20:
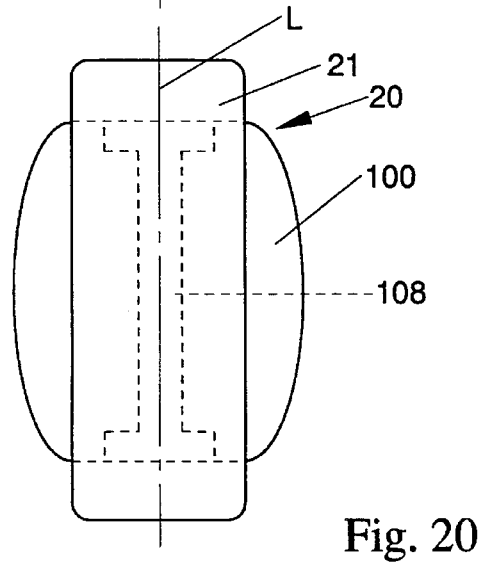
FIG. 20 is a plan view of a sanitary napkin having an attachment mechanism used to join the panty covering component to the main body portion of the sanitary napkin that is in the form of a block letter "I".

FIG. 19 shows an attachment mechanism 108 that is in the form of two strips that extend in the transverse direction. The strips are on opposite sides of the transverse centerline. These strips are preferably located at the transverse end edges 100D of the panty covering component. FIG. 20 shows an attachment mechanism that is in the form of a block letter "T" which has two strips similar to those shown in FIG. 19 and a central strip that runs down the longitudinal centerline connecting the two transverse strips. The attachment patterns in FIGS. 19 and 20 have the advantage that they can permit the main body portion 21 of the sanitary napkin to decouple from the panty covering component and the central region 32 of the main body portion can also permit the main body portion to bunch inward without pulling the panty covering component inward.

Returning to the discussion of the preferred embodiment shown in FIGS. 1–5, there are several factors which were taken into account in providing such a product. When such an embodiment is provided with a main body portion that is generally inextensible, a key dimension to the proper functioning of the panty covering component embodiment shown therein is the dimension $D_2$ (shown in FIG. 1). The dimension $D_2$ can be measured longitudinally or laterally, as shown in FIG. 1. The dimension $D_2$ is the distance from the place where: (a) the isolation element 102 is bonded to any inextensible components of the sanitary napkin, point P, to the place where (b) the isolation element 102 is bonded to the sheet of extensible material 100, point Q. (In this embodiment, if the main body portion comprises inextensible or less extensible components, the isolation element 102 would be bonded to any inextensible components of the sanitary napkin at the seam 90 around the perimeter of the sanitary napkin.)

The dimension $D_2$ is important because it affects the amount that the extensibility properties of the sheet of extensible material 100 and the main body portion of the sanitary napkin 20 can be decoupled. The dimension $D_2$ required for a particular sanitary napkin depends on the relative extensibility of the materials comprising all of the relevant portions of the sanitary napkin. The portions of the sanitary napkin relevant to the dimension $D_2$ include, but are not limited to the inextensible components, the sheet of extensible material 100, and the isolation element 102. For instance, if the isolation element 102 is extremely extensible, the isolation element 102 will not need a great $D_2$ dimension to create a sufficient amount of slack between the sheet of extensible material and the inextensible components.

The dimension $D_2$ will also depend on the dimensions of the attachment mechanism used to attach the sanitary napkin 20 to the wearer's panties. This is because the slack material can also be present in the portion of the sheet of extensible material 100 between the edge of the panty fastener and the place where the sheet of extensible material 100 is joined to the isolation element 102. Preferably, in the embodiment described herein, $D_2$ is greater than or equal to about 5 mm, more preferably greater than or equal to about 10 mm, more preferably, and most preferably is greater than or equal to about 15 mm. The upper limit on $D_2$ is as follows. $D_2$ is preferably not so large that point Q extends past the intersection of the centerlines of the sanitary napkin, point I.

Figure 4:
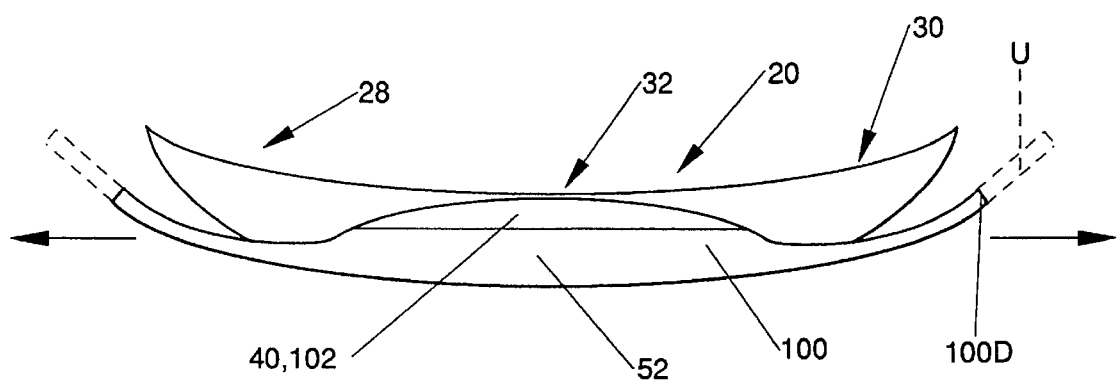
FIG. 4 is a side view of the sanitary napkin shown in FIG. 1 (taken from an angle similar to that of FIG. 3) in an in-use configuration.
Figure 5:
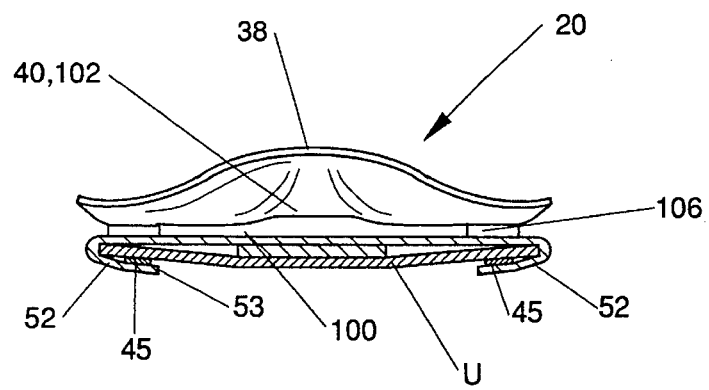
FIG. 5 is an end view of the sanitary napkin shown in FIG. 1 in an in-use configuration.

FIGS. 4 and 5 show what happens when the sanitary napkin 20 with the panty covering component 100 shown in FIGS. 1–3 is stretched. The sheet of stretchable material 100 stretches with the wearer's undergarments U. FIG. 4 shows that the end regions 28 and 30 of the sanitary napkin 20 will curve upward when the sanitary napkin is viewed from the side. This will provide the sanitary napkin an overall curved longitudinal profile. FIG. 5 shows that the sanitary napkin 20 is saddle-shaped when viewed from the end. The particular curvature shown in FIGS. 4 and 5 results from the configuration of the attachment mechanism between the sheet of extensible material 100 and the isolation element 102. Other attachment mechanisms may be used to create other stretched configurations.

The panty covering component (as noted above) automatically wraps around the sides of the wearer's panties by the simple action of the wearer pulling up her panties. There are several additional matters which should be kept in mind relating to the features of the panty covering component.

First, placing a sanitary napkin having conventional flaps in a pair of panties and pulling up the panties will not consistently provide the automatic sustained wraparound feature of the present invention. There are several reasons for this. The conventional flaps are not extensible, so they will not conform to the panties. Conventional flaps are not provided with a low return force and a high fold retention, so that in cases where conventional flaps wrap around the panties, they do not consistently stay. In addition, conventionally-sized flaps will have excess flap material that hangs down underneath the panties during wear. This material can move around excessively underneath the panties. The side wrapping elements of the present invention, on the other hand, have a span that is ideally just wide enough to wrap around the elastic-containing edges of the panties, but no wider. The absence of material hanging down under the panties, combined with the extensibility of the same, reduces any tendency for the side wrapping elements to bunch longitudinally inward during wear.

The second matter which should be kept in mind is that the portions of the panty covering component to the longitudinal ends of the side wrapping elements that do not wrap around the edges of the panties can also serve an important function. These portions, end portions (or "non-wrapping portions") are shown as 52' in FIG. 1. The sanitary napkin is preferably constructed so these non-wrapping portions 52' can naturally work their way into the area of the wearer's leg crease to provide a gasketing effect against the wearer's body. This is believed to provide the wearer with extra protection from soiling of the wearer's panties (even in these areas) where the panty covering component does not cover the panty elastics. This is particularly true when the panty covering component is between about 150–200 mm long, or up to about 90% of the length of the main body portion for sanitary napkins having main body portions longer than 200 mm.

The gasketing benefits f the non-wrapping portions 52' is believed to be attributable to several factors associated with the construction of the sanitary napkin. When the side wrapping elements 52 are wrapped around the edges of the panties, the non-wrapping portions 52' are held in tension. The non-wrapping portions 52' are held at one end by the panty elastic, and at the other end by the smaller adhesive areas 106 in the corners 27 of the sanitary napkin. This causes the non-wrapping elements to stand more upright to form these gasket-like structures, rather than to simply flop over.

The benefits provided by the non-wrapping portions are enhanced when the panty covering component has a nonwoven body-facing side. When the panty covering component has a nonwoven body-facing side, this provides the panty covering component with a "skin friendly" surface that is desirable when the non-wrapping portions serve their gasketing function.

The panty covering component, as noted above, may provide an extensible (or stretchable) interactive connection between the main body portion of the sanitary napkin and the wearer's undergarments. The panty covering component 100 is particularly useful in providing a generally inextensible sanitary napkin with the ability to adapt to the stretching of the wearer's undergarments. The panty covering components are also useful in providing the other benefits of extensibility described herein. The panty covering component 100 can be stretchable, and therefore, it can be considered to be a variety of a stretchable attachment device as described in U.S. patent application Ser. No. 07/915,133 (PCT Publication No. 93/01785).

F. Fasteners for Attaching the Sanitary Napkin to the Wearer's Panties.

The garment surface 20B of the sanitary napkin 20 (e.g., the garment surface 100B of the panty covering component) may include fasteners (or "means for attaching the sanitary napkin to the undergarment of the wearer" or "attaching means") 44.

FIGS. 2 and 3 show the central pad fastener 44 which is adapted to secure the main body portion 21 of the sanitary napkin 20 to the crotch region of an undergarment. Fasteners comprising adhesives have been found to work well for this purpose. Any adhesive or glue used in the art for such purposes can be used, with pressure-sensitive adhesives being preferred. Suitable adhesives are Century A-305-IV manufactured by the Century Adhesives Corporation, Instant Lock 34-2823 manufactured by the National Starch Company, 3 Sigma 3153 manufactured by 3 Sigma, and Fuller H-2238ZP manufactured by the H.B. Fuller Co. Suitable adhesive fasteners are also described in U.S. Pat. No. 4,917,697.

The central pad fastener 44 can be in many possible configurations depending on the characteristics desired for the sanitary napkin. FIGS. 2 and 3 show one preferred arrangement which utilizes a longitudinally oriented zone of extensible adhesive centered about the longitudinal centerline L. Other suitable fastener configurations are shown in PCT International Patent Publication No. WO 92/04000 entitled "Shape and Adhesive Fastening Means for an Absorbent Article" published in the name of Papa, et al. on Mar. 19, 1992; PCT Publication No. WO 93/01783 published in the name of Olsen, et al., and in PCT Publication No. WO 93/01785 published in the name of Osborn, et al.

It should be understood that if it is desired to make the component that forms the garment surface of the sanitary napkin (and any overlying components) extensible in the wearer's panties, the particular adhesive configurations that can be used depend on whether extensible or inextensible adhesives are used. The portion of the sanitary napkin on which extensible adhesives are located will be extensible. Sanitary napkins containing inextensible adhesives will typically only be capable of extension between the inextensible adhesive patches. Therefore, if inextensible adhesives are used, they are preferably applied in intermittent patterns, including but not limited to intermittent dots, intermittent strips, and the like, to permit the sanitary napkin to extend between adhesive patches. If, on the other hand, the adhesive is extensible, the adhesive can be applied in continuous or intermittent patterns in the above configurations (and other configurations). If the adhesives are extensible, they preferably extend approximately the same amounts as the sanitary napkin as set forth in Table 1.

Suitable extensible adhesives include extensible adhesives, per se, and extensible adhesive/backsheet combinations. Any extensible adhesives known in the art can be used. Suitable extensible adhesive/backsheet combinations include, but are not limited to non-extensible adhesive used on an extensible backsheet material such as 3 Sigma 2474 available from Anchor Continental, Inc., 3 Sigma Division, of Covington, Ohio; elastically stretchable adhesive films such as Findley adhesive 198-338, or an elastically stretchable adhesive film known as 3M XPO-0-014 available from the Minnesota Mining and Manufacturing Company of St. Paul, Minn.; or spray adhesives such as 3M adhesive 1442 on a low modulus elastic film.

In addition, other types of fasteners can be used instead of, or in addition to adhesives. These other types of fasteners are preferably arranged in patterns similar to those in the patent publications referred to above. Such fasteners include, but are not limited to conventional VELCRO hook material, the fasteners described in: U.S. Pat. No. 4,946,527 issued to Battrell on Aug. 7, 1990; U.S. Pat. Nos. 5,058,247 and 5,116,563 issued to Thomas, et al. on Oct. 22, 1991 and May 26, 1992, respectively; and EPO Patent Application Publication No. 0 381 087 published Aug. 8, 1990; or, high coefficient of friction foams and other high coefficient of friction materials in the same category as those described in U.S. Pat. No. 4,166,464 issued to Korpman, U.S. Pat. No. 4,834,739 issued to Linker, III, et al., and U.S. Pat. No. 5,011,480 issued to Gossens, et al. These fasteners may also be made extensible as described in U.S. patent application Ser. No. 07/915,133 (PCT Publication No. 93/01785).

The side wrapping elements 52, as noted above, should wrap and stay without being provided with fasteners to secure the same to the panties. However, embodiments of the present invention may have optional fasteners thereon for additional security. The optional side wrapping element fasteners 45 can be any of the types of fastening materials specified herein.

The optional side wrapping element fasteners 45 assist the side wrapping elements 52 in staying in position after they are wrapped around the edges of the crotch portion of the panty. The side wrapping element fasteners 45 may be located on the garment surface of side wrapping elements 52, adjacent the distal edges 53 of the side wrapping elements 52 (i.e., the end of the side wrapping elements 52 farthest away from the longitudinal centerline L of the sanitary napkin 20), or at various other locations on the side wrapping elements.

Figure 21:
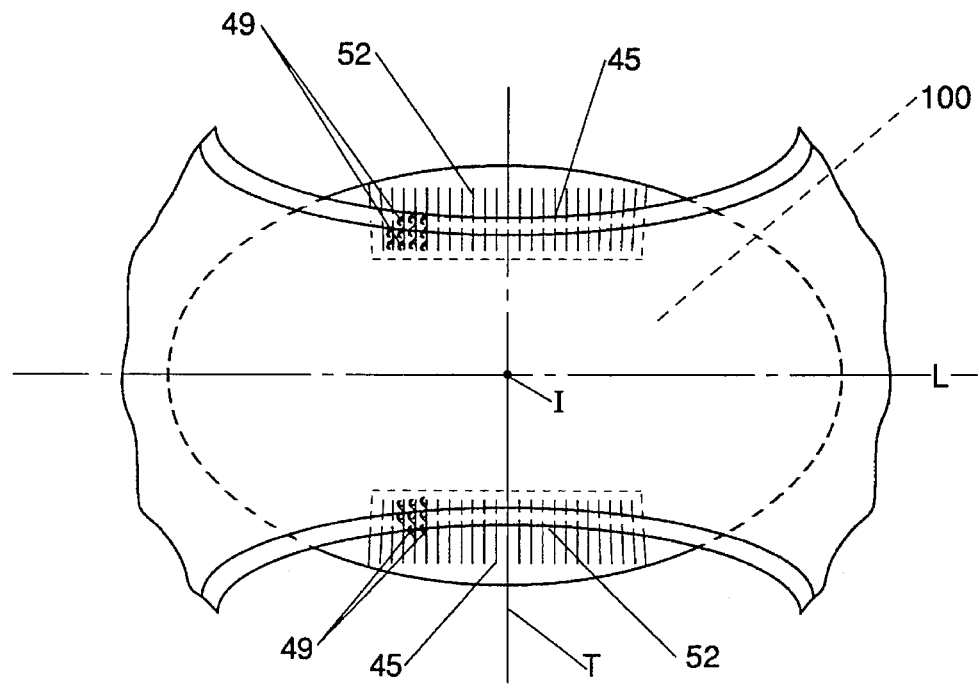
FIG. 21 is a bottom plan view of a panty covering component having hook-like mechanical fasteners distributed radially on portions thereof, as shown in place in a section of a panty crotch.

In one alternative embodiment, as shown in FIG. 21, the side wrapping elements 52 are provided with side wrapping elements in the form of strips of hook material 45 or other mechanical fastener material 45. In this preferred embodiment, the holes 49 on the strips of hook material 45 are distributed in a radial pattern. The hooks can be oriented in a particular direction for improved gripping properties. Preferably, in the embodiment in FIG. 21, the mouths of the hooks are oriented so that they face the intersection of the longitudinal and transverse centerlines.

The use of mechanical fasteners on absorbent articles is believed to be particularly beneficial, due to their tendency to reduce the effect of the shearing forces exerted on the garment surface 20B of the sanitary napkin 20 by the wearer's panties moving in response to the wearer's body motions. Mechanical fasteners that engage the fabric of the wearer's panties will move with the panties, reducing the problems caused by these shearing forces. The mechanical fastening devices have engaging elements 49 that preferably engage the fabric (typically, the yarns of a knit or woven fabric) covering the panty leg elastics. The mechanical fastening devices may engage the fabric covering the top of the wearer's panty elastics, the fabric covering the sides of the panty elastics, or the fabric covering the bottom of the panty elastics.

Figure 22:
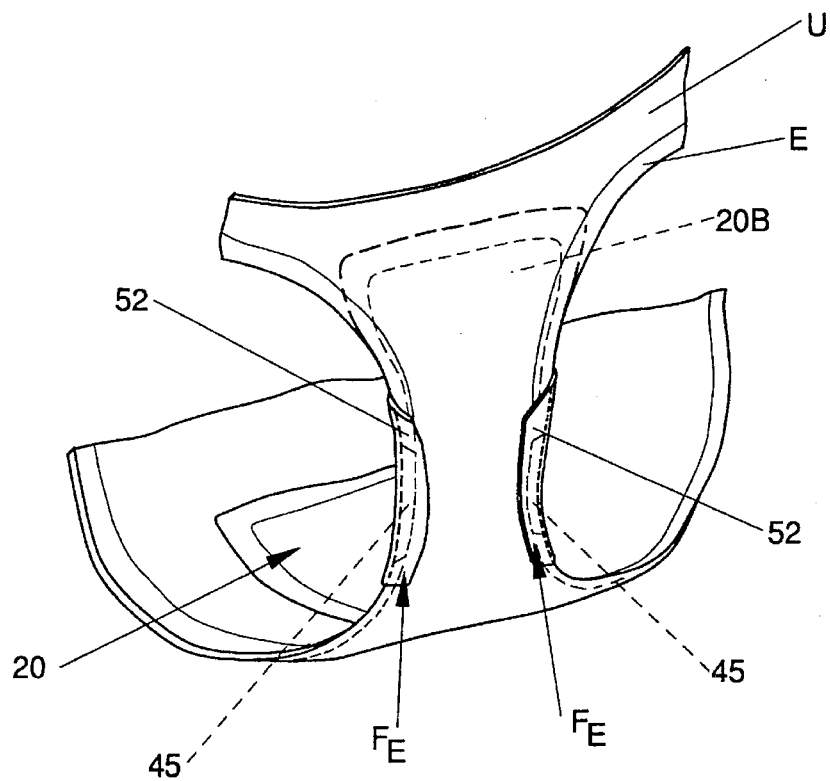
FIG. 22 is a perspective view of a portion of a panty with the sanitary napkin of the present invention in place therein.

The use of mechanical attachment elements at or near the panty elastics and at other places, such as at the end edges 24 of the main body portion of the sanitary napkin 20, also eliminates several problems associated with the use of adhesive fasteners alone. Mechanical fasteners are not subject to the problem of adhesives sticking to the wearer's body hair. They are also not subject to the problem of the adhesives become unattached and causing the sanitary napkin folding back and stick to itself when the panty and panty elastics move and stretch. Further, as shown in FIG. 22, the leg elastics of the wearer's panties, E, are stretched when the panties are put on by the wearer. This causes the elastics to exert forces $F_E$ against the wearer's body. These forces provide a normal force component relative to the portions of the side wrapping elements 52 that are against the wearer's body. The normal force component can be used to cause mechanical or frictional attachment means to be more effective. Normal forces may aid mechanical fasteners having hook-like elements in penetrating and hooking onto the fabric of the wearer's panties. Ideally, the normal forces will cause the hooks to automatically engage the panty fabric with little or no effort needed on the part of the wearer to press the hooks into the panties.

Figure 23:
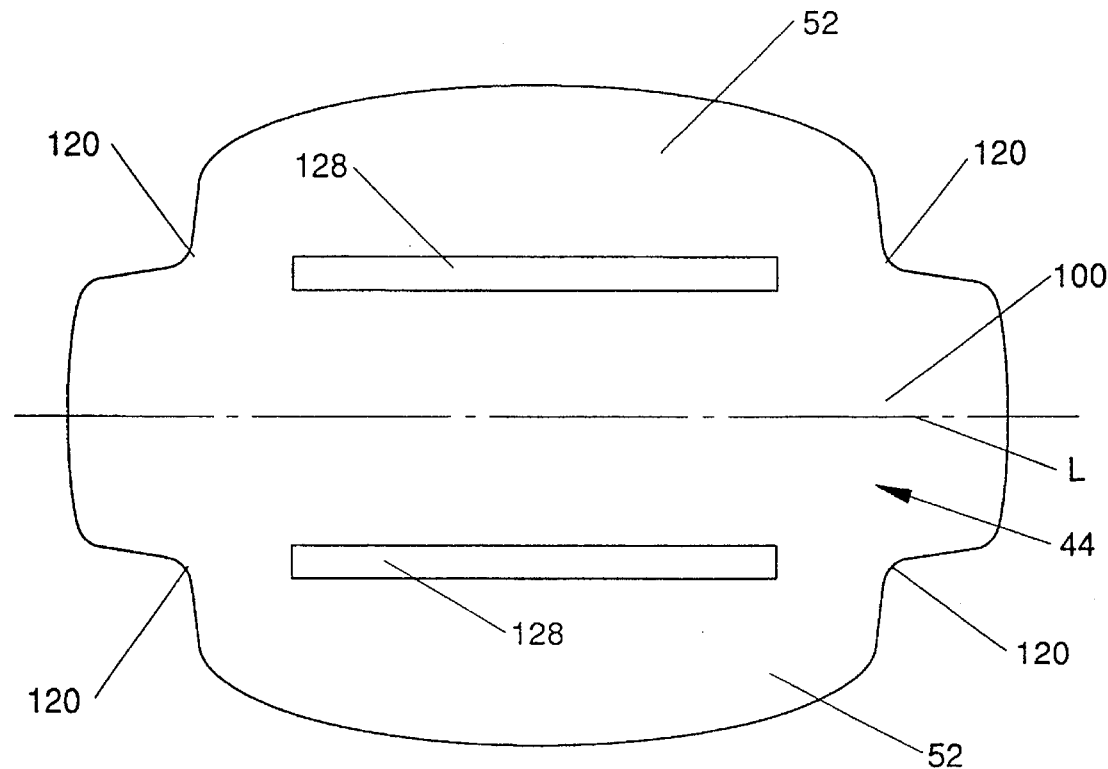
FIG. 23 is a plan view of an alternative embodiment of the panty covering component of the present invention.
Figure 24:
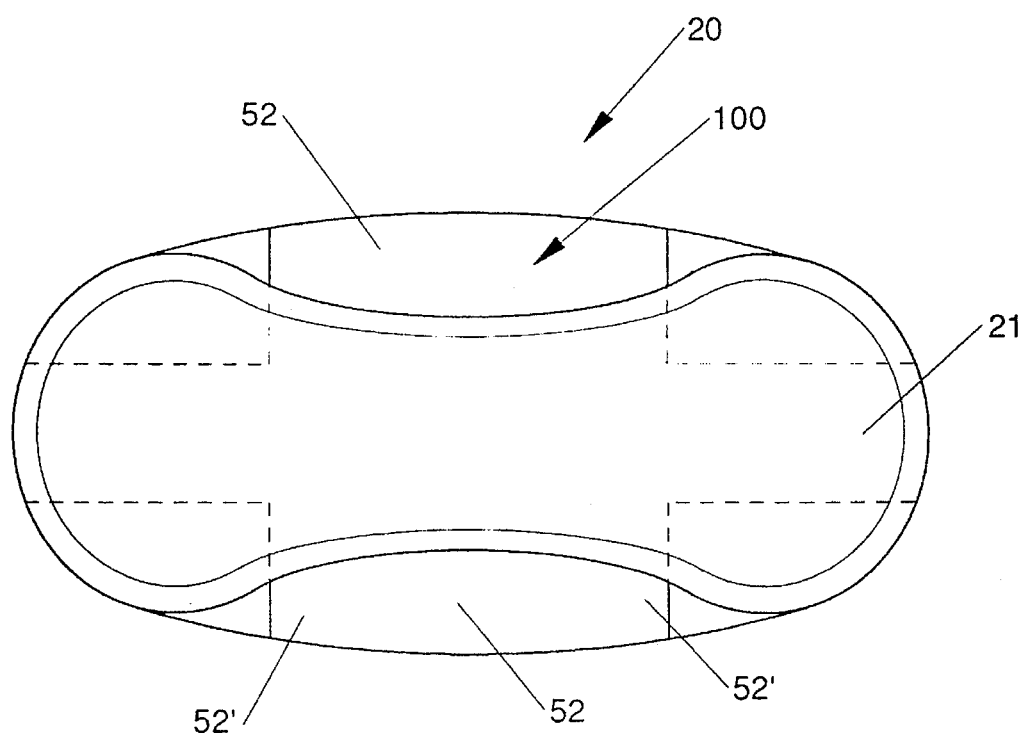
FIG. 24 is a top plan view of a sanitary napkin having a panty covering component that is generally inextensible with the exception of zones in the corners of the panty covering component.

In another alternative embodiment shown in FIG. 23, the panty covering component 100 has indentations at its four corners 120 to allow the panty covering component to adjust to the shape of the wearer's undergarments. This embodiment is especially useful when the sanitary napkin is worn with menstrual shorts of the type typically worn by Japanese women. The indentations also allow the panty covering component to assist the side wrapping elements in flipping underneath the crotch region of the wearer's undergarments. The panty covering component 100 shown in FIG. 23 is preferably provided with an overall multi-directional extensibility. The panty covering component is also preferably provided with an adhesive fastener that covers the entire garment side of the same with the exception of two longitudinally oriented zones 128 which are adhesive-free. The adhesive-free zones 128 prevent the side wrapping elements 52 from folding over onto and sticking to other portions of the panty covering component after the release paper is removed from the back of the panty covering component. Optionally, the adhesive-free areas can be provided with a releasable material to further reduce any tendency for the side wrapping elements to stick to these portions of the panty covering component.

Before the sanitary napkin 20 is placed in use, if an adhesive fastener is used, the adhesive is typically covered with a removable cover strip or release liner 52 in order to keep the adhesive from sticking to a surface other than the crotch portion of the panty prior to use. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/0, both of which are manufactured by the Akrosil Corporation.

In particularly preferred embodiments, the adhesive fastener 50 is protected with a wrapper that not only covers the adhesive, but also provides both an individually packaged sanitary napkin and a container for disposing the sanitary napkin after use, such as is described in U.S. Pat. No. 4,556,146 issued to Swanson, et al. on Dec. 3, 1985 and in PCT International Publication No. WO 93/09743 entitled "Sanitary Napkin Wrapper and Adhesive Tab Construction for the Same" published in the name of Berg, et al. on May 27, 1993.

The sanitary napkin 20 of the present invention is used by removing any release liner 52 and thereafter placing the sanitary napkin 20 in a panty so that the adhesive (or other fastener) 50 contacts the panty and maintains the sanitary napkin in position within the panty during use.

The following Example further illustrates the practice of the present invention. The following Example, however, is not intended to limit the scope of the absorbent articles encompassed herein.

EXAMPLE

The topsheet 38 is made in accordance with U.S. Pat. No. 4,463,045 and ring rolled to provide it with longitudinal extensibility. The absorbent core 42 is a superabsorbent material laminate as described above which is slitted or partially slitted for longitudinal extensibility. FIG. 8 shows an absorbent core 42 that is slit at the end regions 28 and 30, but not at the central region 32. The backsheet 40 is an extensible adhesive film known as Formula #198-338 manufactured by the Findley Adhesives Company of Wauwatosa, Wisconsin. The sanitary napkin 20 also includes a creped BOUNTY (TM) paper towel layer and several layers of extensible, highly-oriented spunlaced polyester nonwoven material obtained from Veratec Inc., a Division of International Paper Company, of Walpole, Mass. One layer of Veratec spunlaced nonwoven having a basis weight of 19 g/yd$^2$ and two layers having a basis weight of 30 g/yd$^2$ are used. This material is extensible in the lateral direction as it is unrolled.

Assembly of the main body portion of the sanitary napkin is as follows. Cut the ring-rolled topsheet to size. Place a template on the bottom side of the topsheet and apply Findley 4031 adhesive in a spiral pattern. Lay the Findley backsheet with a protective release paper attached on flat surface. Place the slitted absorbent gelling material (AGM) laminate core on the Findley backsheet. Center the creped BOUNTY tissue (shaped similarly to the topsheet) over the laminate core. Place the topsheet over the creped tissue. Secure the components and smooth at edges. Roll the edges to seal. Peel the release paper from the back of the backsheet. Tear and remove in 2 or 3 pieces, then place the Veratec nonwoven material having the lower basis weight (19 g/yd$^2$) on the exposed adhesive on the backsheet (oriented so the nonwoven is extensible in the longitudinal direction). Spray the topsheet with 0.01 g. PEGOSPERSE surfactant available from Lonza, Inc., Williamsport, Pa.

Assembly of the panty covering component is a follows. Form a laminate of the Findley extensible adhesive between the two layers of higher basis weight nonwoven (30 g/yd$^2$). Apply panty fastening adhesive.

Assembly of the complete sanitary napkin is as follows. Bond the isolation layer to the main body portion around the perimeter of the main body portion with the 0.25 inch wide Findley adhesive. Trim the isolation layer to the same shape as the main body portion. Bond this assembly to the panty covering component with the 1.5 inch wide Findley adhesive. The adhesive is centered along the longitudinal centerline of the main body portion. Cut the panty covering component to shape.

The specifications of the finished product are as follows:

| Main Body Portion | |
| --- | --- |
| Parameters of Main Body Portion | Specifications |
| Pad weight (g) | 8.50 ± 0.18 |
| Core weight (g) laminate | 2.54 ± 0.09 |
| Pad length (m) | 232 ± 4 |
| Core length (mm) laminate | 201 ± 1 |
| Pad width at center (m) | 85 ± 1 |
| Core width at center (m) | 65 ± 1 |
| Pad caliper (in. at 0.13 psi) | 0.11 ± 0.01 (2.9 m) |
| Core caliper (in. at 0.13 psi) | 0.074 ± 0.003 |
| Components of Main Body Portion | Specifications |
| Polyethylene formed-film topsheet (per U.S. | 9" × 5" |

-continued

| | |
|---|---|
| Pat. No. 4,463,045; ring rolled) | |
| Findley extensible adhesive film backsheet (Formula #198-338) | –9" × 5" |
| Creped BOUNTY paper towel | Shaped* |
| PFA (panty fastening adhesive) | None |
| PEGOSPERSE | 0.01 g |
| Veratec spunlaced nonwoven (19 g/yd²) | 9" × 5" |
| AGM slit core non-slit center; total core weight 2.5 g; contains 0.7 g AGM | 65 m × 193 mm with 2 ¾" non-slit center |
| Findley 4031 (adhesive) | 0.05 g |

Isolation Layer

| Parameters of Isolation Layer | Specifications |
|---|---|
| Length | 232 ± 4 |
| Width of Center | 85 ± 1 |
| Components of Isolation Layer | Specifications |
| Veratec spunlaced nonwoven (19 g/yd²) | 9" × 5" |
| Bond to panty covering component | 9" × 1.50" |
| Bond to main body portion (around perimeter) | 30" × 0.25" |

Panty Covering Component

| Parameters of Panty Covering Component | Specifications |
|---|---|
| Length (mm) | 232 ± 4 |
| Width | 108 ± 2 |
| Components of Panty Covering Component | Specifications |
| Veratec spunlaced nonwoven (30 g/yd² - 2 layers) | 9" × 5" |
| Findley extensible adhesive film | 9" × 5" |
| PFA (panty fastening adhesive) | 8" × 2.5" |
| Release paper | As needed |

G. Other Alternative Embodiments.

While several preferred sanitary napkin embodiments have been described, numerous other sanitary napkin embodiments are disclosed in the literature. These could be provided with the panty covering component of the present invention. Some of such sanitary napkins are described in U.S. Pat. Nos. 5,009,653 and 4,950,264, issued to Osborn on Apr. 23, 1991 and Aug. 21, 1990, respectively, and in U.S. patent application Ser. No. 07/915,202, entitled "Curved, Shaped Absorbent Article" filed in the name of Johnson, et al. (PCT Publication No. WO 93/01781).

The terms "panty liner" or "pantiliner" refer to absorbent articles that are less bulky than sanitary napkins which are generally worn by women between their menstrual periods. Suitable absorbent articles in the form of pantiliners are disclosed in U.S. Pat. No. 4,738,676 entitled "Pantiliner" issued to Osborn on Apr. 19, 1988.

The term "incontinence article" refers to pads, undergarments (pads held in place by a suspension system of same type, such as a belt, or the like), inserts for absorbent articles, capacity boosters for absorbent articles, briefs, bed pads, and the like, regardless of whether they are worn by adults or other incontinent persons. Suitable incontinent articles that can be provided with the panty covering components described herein are disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat. No. 4,704,115; U.S. Pat. No. 4,909,802 issued to Ahr, et al.; U.S. Pat. No. 4,964,860 issued to Gipson, et al. on Oct. 23, 1990; and in U.S. patent application Ser. Nos. 07/637,090 and 07/637,571 filed respectively by Noel, et al. and Feist, et al. on Jan. 3, 1991 (PCT Publication Nos. WO 92/11830 and WO 92/11831, respectively, both published on Jul. 23, 1992).

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

While particular embodiments of the present invention have been illustrated and described, it would be obvious to those skilled in the art that various other changes and modifications can be made without departing from the spirit and scope of the invention.

What is claimed is:

1. An absorbent article for wearing in a crotch region of an undergarment, said absorbent article having a longitudinal dimension extending in a longitudinal direction and a transverse dimension extending in a transverse direction, a longitudinal centerline, and a transverse centerline, said absorbent article comprising:

a main body portion comprising an absorbent core, said main body portion having a body-facing side, a garment-facing side, and a pair of longitudinal side edges; and an undergarment covering component, said undergarment covering component being joined to the garment-facing side of said main body portion inboard of the longitudinal side edges of said main body portion at affixation points and being otherwise unattached to said main body portion laterally outboard of at least some of said affixation points, said undergarment covering component comprising a pair of side wrapping elements for folding around a side of a crotch region of an undergarment, said side wrapping elements extending laterally outward beyond the longitudinal side edges of said main body portion a distance of less than one-half the width of said main body portion to distal edges, wherein at least a portion of said undergarment covering component is extensible generally in the longitudinal direction between said affixation points and said distal edges of said side wrapping elements when said side wrapping elements are folded around a side of a crotch portion of an undergarment, and said extensible portion of said undergarment covering component has a return force of less than or equal to about 100 grams.

2. The absorbent article of claim 1 wherein said return force is less than or equal to about 50 grams.

3. The absorbent article of claim 2 wherein said return force is less than or equal to about 25 grams.

4. An absorbent article for wearing in a crotch region of an undergarment, said absorbent article having a longitudinal dimension extending in a longitudinal direction and a transverse dimension extending in a transverse direction, a longitudinal centerline, and a transverse centerline, said absorbent article comprising:

a main body portion comprising an absorbent core, said main body portion having a body-facing side, a garment-facing side, and a pair of longitudinal side edges; and undergarment covering component, said undergarment covering component being joined to the garment-facing side of said main body portion inboard of the longitudinal side edges of said main body portion at affixation points and being otherwise unattached to said main body portion laterally outboard of at least some of said affixation points, said undergarment covering component comprising a pair of side wrapping elements for folding around a side of a crotch region of an undergarment, said side wrapping elements extending laterally outward beyond the longitudinal side edges of said main body portion a distance of less than one-half the width of said main body portion to distal edges, wherein at least a portion of said undergarment covering component is extensible generally in the longitudinal direction between said affixation points and said distal edges of said side wrapping elements when said side wrapping elements are folded around a side of a crotch portion of an undergarment, wherein said extensible portions have a set of greater than or equal to about 10%.

5. The absorbent article of claim 4 wherein said extensible portions have a set of greater than or equal to about 20%.

6. An absorbent article for wearing in a crotch region of an undergarment, said absorbent article having a longitudinal dimension extending in a longitudinal direction and a transverse dimension extending in a transverse direction, a longitudinal centerline, and a transverse centerline, said absorbent article comprising:

a main body portion comprising an absorbent core, said main body portion having a body-facing side, a garment-facing side, and a pair of longitudinal side edges; and undergarment covering component, said undergarment covering component being joined to the garment-facing side of said main body portion inboard of the longitudinal side edges of said main body portion at affixation points and being otherwise unattached to said main body portion laterally outboard of at least some of said affixation points, said undergarment covering component comprising a pair of side wrapping elements for folding around a side of a crotch region of an undergarment, said side wrapping elements extending laterally outward beyond the longitudinal side edges of said main body portion a distance of less than one-half the width of said main body portion to distal edges, wherein at least a portion of said undergarment covering component is extensible generally in the longitudinal direction between said affixation points and said distal edges of said side wrapping elements when said side wrapping elements are folded around a side of a crotch portion of an undergarment, wherein said side wrapping elements each have a resistance to edge compression of greater than or equal to about 5 grams force.

7. An absorbent article for wearing in a crotch region of an undergarment, said absorbent article having a longitudinal dimension extending in a longitudinal direction and a transverse dimension extending in a transverse direction, a longitudinal centerline, and a transverse centerline, said absorbent article comprising:

a main body portion comprising an absorbent core, said main body portion having a body-facing side, a garment-facing side, and a pair of longitudinal side edges; and undergarment covering component, said undergarment covering component being joined to the garment-facing side of said main body portion inboard of the longitudinal side edges of said main body portion at affixation points and being otherwise unattached to said main body portion laterally outboard of at least some of said affixation points, said undergarment covering component comprising a pair of side wrapping elements for folding around a side of a crotch region of an undergarment, said side wrapping elements extending laterally outward beyond the longitudinal side edges of said main body portion a distance of less than one-half the width of said main body portion to distal edges, wherein at least a portion of said undergarment covering component is extensible generally in the longitudinal direction between said affixation points and said distal edges of said side wrapping elements when said side wrapping elements are folded around a side of a crotch portion of an undergarment, wherein said side wrapping elements each have a resistance to edge compression of greater than or equal to about 10 grams force.

8. An absorbent article for wearing in a crotch region of an undergarment, said absorbent article having a longitudinal dimension extending in a longitudinal direction and a transverse dimension extending in a transverse direction, a longitudinal centerline, and a transverse centerline, said absorbent article comprising:

a main body portion comprising an absorbent core, said main body portion having a body-facing side, a garment-facing side, and a pair of longitudinal side edges; and a pair of side wrapping elements for folding at least partially around a side of a crotch region of an undergarment, said side wrapping elements being joined to the garment-facing side of said main body portion inboard of the longitudinal side edges of said main body portion at affixation points and being otherwise unattached to said main body portion laterally outboard of at least some of said affixation points, said side wrapping elements extending laterally outward beyond the longitudinal side edges of said main body portion, wherein at least a portion of said side wrapping elements is extensible between said affixation points and said distal edges of said side wrapping elements when said side wrapping elements are folded around a side of a crotch portion of an undergarment, and said extensible portion of said side wrapping elements has a return force of less than or equal to about 100 grams.

9. A sanitary napkin for wearing in a crotch region of a pair of panties, said sanitary napkin having a longitudinal dimension extending in a longitudinal direction and a transverse dimension extending in a transverse direction, said sanitary napkin comprising:

a main body portion comprising an absorbent core, said main body portion having a body-facing side, a garment-facing side, and a pair of longitudinal side edges; and a pair of side wrapping elements for folding at least partially around a side of a crotch region of an undergarment, said side wrapping elements being joined to the garment-facing side of said main body portion at affixation points that are inboard of the longitudinal side edges of said main body portion and being otherwise unattached to said main body portion laterally outboard of at least some of said affixation points, said side wrapping elements extending laterally outward beyond the longitudinal side edges of said main body portion, wherein at least a portion of said side wrapping elements is extensible when said side wrapping elements are folded at least partially around a side of a crotch portion of a pair of panties, and said extensible portions of said side wrapping elements have a return force of less than or equal to about 100 grams.

10. A sanitary napkin for wearing in a crotch region of a pair of panties, said sanitary napkin having a longitudinal dimension extending in a longitudinal direction and a transverse dimension extending in a transverse direction, said sanitary napkin comprising:

a main body portion comprising an absorbent core, said main body portion having a body-facing side, a garment-facing side, and a pair of longitudinal side edges; and a pair of side wrapping elements for folding at least partially around a side of a crotch region of a pair of panties, said side wrapping elements being joined to the garment-facing side of said main body portion inboard of the longitudinal side edges of said main body portion at affixation points and being otherwise unattached to said main body portion laterally outboard of at least some of said affixation points, said side wrapping elements extending laterally outward beyond the longitudinal side edges of said main body portion a distance of less than one-half the width of said main body portion to distal edges, wherein at least a portion of each of said side wrapping elements is extensible generally in the longitudinal direction in an amount between about 10% and about 40% under any force within the range of between about 50 grams and about 1,500 grams between said affixation points and said distal edges of said side wrapping elements when said side wrapping are folded when said side wrapping elements are folded at least partially around a side of a crotch portion of a pair of panties and said extensible portions of said side wrapping elements have a return force of less than or equal to about 100 grams.

11. An absorbent article for wearing in a crotch region of an undergarment, said absorbent article having a longitudinal dimension extending in a longitudinal direction and a transverse dimension extending in a transverse direction, a longitudinal centerline, and a transverse centerline, said absorbent article comprising:

a main body portion comprising an absorbent core, said main body portion having a body-facing side, a garment-facing side, and a pair of longitudinal side edges; and a pair of side wrapping elements for folding at least partially around a side of a crotch region of an undergarment, said side wrapping elements being joined to the garment-facing side of said main body portion inboard of the longitudinal side edges of said main body portion at affixation points and being otherwise unattached to said main body portion laterally outboard of at least some of said affixation points, said side wrapping elements extending laterally outward beyond the longitudinal side edges of said main body portion, wherein at least a portion of said side wrapping elements is extensible generally in the longitudinal direction between said affixation points and said distal edges of said longitudinal side portions when said side wrapping elements are folded at least partially around a side of a crotch portion of an undergarment, and said extensible portion of said side wrapping elements has a set of greater than or equal to about 10%.

12. A sanitary napkin for wearing in a crotch region of a pair of panties, said sanitary napkin having a longitudinal dimension extending in a longitudinal direction and a transverse dimension extending in a transverse direction, said sanitary napkin comprising:

a main body portion comprising an absorbent core, said main body portion having a body-facing side, a garment-facing side, and a pair of longitudinal side edges; and a pair of side wrapping elements for folding at least partially around a side of a crotch region of a pair of panties, said side wrapping elements being joined to the garment-facing side of said main body portion inboard of the longitudinal side edges of said main body portion at affixation points and being otherwise unattached to said main body portion laterally outboard of at least some of said affixation points, said side wrapping elements extending laterally outward beyond the longitudinal side edges of said main body portion a distance of less than one-half the width of said main body portion to distal edges, wherein at least a portion of each of said side wrapping elements is extensible generally in the longitudinal direction in an amount between about 10% and about 40% under any force within the range of between about 50 grams and about 1,500 grams between said affixation points and said distal edges of said side wrapping elements when said side wrapping elements are folded at least partially around a side of a crotch portion of a pair of panties and said extensible portions of said side wrapping elements have a set of greater than or equal to about 10%.

13. An absorbent article for wearing in a crotch region of an undergarment, said absorbent article having a longitudinal dimension extending in a longitudinal direction and a transverse dimension extending in a transverse direction, a longitudinal centerline, and a transverse centerline, said absorbent article comprising:

a main body portion comprising an absorbent core, said main body portion having a body-facing side, a garment-facing side, and a pair of longitudinal side edges; and a pair of side wrapping elements for folding at least partially around a side of a crotch region of an undergarment, said side wrapping elements being joined to the garment-facing side of said main body portion inboard of the longitudinal side edges of said main body portion at affixation points and being otherwise unattached to said main body portion laterally outboard of at least some of said affixation points and extending laterally outward beyond the longitudinal side edges of said main body portion to a distal edge, wherein at least a portion of said side wrapping elements is extensible when said side wrapping elements are folded at least partially around a side of a crotch portion of an undergarment and said side wrapping elements have a resistance to edge compression of greater than or equal to about 5 grams force.

14. A sanitary napkin for wearing in a crotch region of a pair of panties, said sanitary napkin having a longitudinal dimension extending in a longitudinal direction and a transverse dimension extending in a transverse direction, said sanitary napkin comprising:

a main body portion comprising an absorbent core, said main body portion having a body-facing side, a garment-facing side, and a pair of longitudinal side edges; and a pair of side wrapping elements for folding at least partially around a side of a crotch region of an undergarment, said side wrapping elements being joined to the garment-facing side of said main body portion at affixation points that are inboard of the longitudinal side edges of said main body portion and being otherwise unattached to said main body portion laterally outboard of at least some of said affixation points, said side wrapping elements extending laterally outward beyond the longitudinal side edges of said main body portion, wherein at least a portion of said side wrapping elements is extensible when said side wrapping elements are folded at least partially around a side of a crotch portion of a pair of panties, and said extensible portions of said side wrapping elements have a resistance to edge compression of greater than or equal to about 5 grams force.

15. A sanitary napkin for wearing in a crotch region of a pair of panties, said sanitary napkin having a longitudinal dimension extending in a longitudinal direction and a transverse dimension extending in a transverse direction, a longitudinal centerline, and a transverse centerline, said sanitary napkin comprising:

a main body portion comprising an absorbent core, said main body portion having a body-facing side, a garment-facing side, and a pair of longitudinal side edges; and a pair of side wrapping elements for folding at least partially around a side of a crotch region of a pair of panties, said side wrapping elements being joined to said main body portion inboard of the longitudinal side edges of said main body portion at affixation points and being otherwise unnattached to said main body portion laterally outboard of at least some of said affixation points and extending laterally outward beyond the longitudinal side edges of said main body portion a distance of less than about one-half the width of said main body portion to a distal edge, wherein at least a portion of said side wrapping elements is extensible when said side wrapping elements are folded at least partially around a side of a crotch portion of an undergarment and said side wrapping elements have a resistance to edge compression of greater than or equal to about 5 grams force.

16. A sanitary napkin for wearing in a crotch region of a pair of panties, said sanitary napkin having a longitudinal dimension extending in a longitudinal direction and a transverse dimension extending in a transverse direction, a longitudinal centerline, and a transverse centerline, said sanitary napkin comprising:

a main body portion comprising an absorbent core, said main body portion having a body-facing side, a garment-facing side, and a pair of longitudinal side edges; and a pair of side wrapping elements for folding at least partially around a side of a crotch region of a pair of panties, said side wrapping elements being joined to said main body portion inboard of the longitudinal side edges of said main body portion at affixation points and being otherwise unnattached to said main body portion laterally outboard of at least some of said affixation points and extending laterally outward beyond the longitudinal side edges of said main body portion a distance of less than about one-half the width of said main body portion to a distal edge, wherein at least a portion of said side wrapping elements is extensible between about 10% and about 40% in the longitudinal direction under any force within the range of between about 50 grams and about 1,500 grams when said side wrapping elements are folded at least partially around a side of a crotch portion of a pair of panties, and said extensible portion has a return force of less than or equal to about 100 grams and a set of greater than or equal to about 10%, and said side wrapping elements have a resistance to edge compression of greater than or equal to about 5 grams force.

* * * * *